United States Patent
Huang et al.

(10) Patent No.: US 12,419,709 B2
(45) Date of Patent: Sep. 23, 2025

(54) PASSIVE AND ACTIVE ARM CONTROL SCHEMES WITH SENSOR INTEGRATION TO SUPPORT TELE-OPERATION AND DIRECT MANUAL INTERACTION

(71) Applicant: Auris Health, Inc., Redwood City, CA (US)

(72) Inventors: Yanan Huang, Sunnyvale, CA (US); Ying Mao, San Mateo, CA (US); Nicholas J. Eyre, Redwood City, CA (US); Pouya Sabetian, Foster City, CA (US); Mark A. Lown, Castro Valley, CA (US); Jason Tomas Wilson, Redwood City, CA (US)

(73) Assignee: Auris Health, Inc., Santa Clara, CA (US)

( * ) Notice: Subject to any disclaimer, the term of this patent is extended or adjusted under 35 U.S.C. 154(b) by 1154 days.

(21) Appl. No.: 17/164,496

(22) Filed: Feb. 1, 2021

(65) Prior Publication Data
US 2021/0298850 A1 Sep. 30, 2021

Related U.S. Application Data

(60) Provisional application No. 63/002,990, filed on Mar. 31, 2020.

(51) Int. Cl.
*A61B 34/35* (2016.01)
*A61B 34/30* (2016.01)
(Continued)

(52) U.S. Cl.
CPC ........ *A61B 34/35* (2016.02); *A61B 2034/301* (2016.02); *A61B 2034/302* (2016.02);
(Continued)

(58) Field of Classification Search
CPC .......... A61B 34/3561; A61B 2034/302; A61B 2034/306; A61B 34/37; A61B 2090/064
(Continued)

(56) References Cited

U.S. PATENT DOCUMENTS

| 5,737,500 A | 4/1998 | Seraji et al. |
| 6,459,926 B1 | 10/2002 | Nowlin et al. |

(Continued)

FOREIGN PATENT DOCUMENTS

| CN | 105338920 | * | 1/2018 | ............. A61B 34/30 |
| WO | WO-9740435 A2 | | 10/1997 | |
| WO | WO-2014152418 A1 | | 9/2014 | |

OTHER PUBLICATIONS

Choi, et al., "A Force/Moment Direction Sensor and Its Application in Intuitive Robot Teaching Task," ICASE: The Institute of Control, Automation and Systems Engineers, Korea, Dec. 2001, vol. 3, No. 4, pp. 236-241.
(Continued)

*Primary Examiner* — Aaron F Roane
(74) *Attorney, Agent, or Firm* — Frost Brown Todd LLP

(57) ABSTRACT

Certain aspects relate to admittance control modes for a robotic surgery system. The admittance control modes can be based on detecting and/or measuring forces (rotational and/or nonrotational) on a robotic arm and moving the robotic arm in response to such interactions. The forces can include direct manual interaction with the robotic arm by a clinician. The movement of the robotic arm can be within a nullspace that maintains the positions of a medical instrument.

20 Claims, 27 Drawing Sheets

(51) Int. Cl.
*A61B 34/37* (2016.01)
*A61B 90/00* (2016.01)

(52) U.S. Cl.
CPC ......... *A61B 2034/306* (2016.02); *A61B 34/37* (2016.02); *A61B 2090/064* (2016.02)

(58) Field of Classification Search
USPC ............................................................ 606/1
See application file for complete search history.

(56) References Cited

U.S. PATENT DOCUMENTS

| | | |
|---|---|---|
| 8,004,229 B2 | 8/2011 | Nowlin et al. |
| 8,749,189 B2 | 6/2014 | Nowlin et al. |
| 8,786,241 B2 | 7/2014 | Nowlin et al. |
| 8,823,308 B2 | 9/2014 | Nowlin et al. |
| 9,687,310 B2 | 6/2017 | Nowlin et al. |
| 10,111,719 B2 | 10/2018 | Yates et al. |
| 10,123,844 B2 | 11/2018 | Nowlin et al. |
| 10,194,998 B2 | 2/2019 | Nowlin et al. |
| 10,512,514 B2 | 12/2019 | Nowlin et al. |
| 10,835,153 B2 | 11/2020 | Rafii-Tari et al. |
| 11,026,758 B2 | 6/2021 | Mintz et al. |
| 2009/0248038 A1 | 10/2009 | Blumenkranz et al. |
| 2011/0264108 A1* | 10/2011 | Nowlin ................. A61B 34/77 606/130 |
| 2017/0128136 A1 | 5/2017 | Post |
| 2019/0105785 A1 | 4/2019 | Meyer et al. |
| 2019/0202066 A1 | 7/2019 | Maret |
| 2020/0405403 A1* | 12/2020 | Shelton, IV ....... A61B 17/3421 |

OTHER PUBLICATIONS

Whitney, "Force Feedback Control of Manipulator Fine Motions," Journal of Dynamic Systems, Measurement and Control, Jun. 1977, pp. 91-97.

International Search Report and Written Opinion for Application No. PCT/IB2021/050798, dated May 7, 2021, 9 pages.

Yen, S.-H. et al., "Development of a virtual force sensor for a low-cost collaborative robot and applications to safety control", Sensor, 2019, vol. 19, No. 11, 2603, internal pp. 1-19 <https://doi.org/10.3390/s19112603>.

International Preliminary Report on Patentability of Application No. PCT/IB2021/050798, dated Oct. 13, 2022, 5 pages.

G. S. Gupta, S. C. Mukhopadhyay, C. H. Messom and S. N. Demidenko, "Master-Slave Control of a Teleoperated Anthropomorphic Robotic Arm With Gripping Force Sensing," in IEEE Transactions on Instrumentation and Measurement, vol. 55, No. 6, pp. 2136-2145, Dec. 2006, doi: 10.1109/TIM.2006.884393.

European Extended Search Report and Written Opinion dated Jul. 16, 2024, for Application No. 21779659.8, 12 pages.

Chinese First Office and Search Report dated Jul. 16, 2025, for Application No. 202180025843.5, 9 pages.

* cited by examiner

PASSIVE AND ACTIVE ARM CONTROL SCHEMES WITH SENSOR INTEGRATION TO SUPPORT TELE-OPERATION AND DIRECT MANUAL INTERACTION

CROSS REFERENCE

This application claims the benefit of priority to U.S. Provisional Application No. 63/002,990, filed on Mar. 31, 2020, the entire contents of which are hereby incorporated by reference.

JOINT RESEARCH AGREEMENT

Subject matter in this application was made by or on behalf of parties to a joint research agreement. The parties to the joint research agreement include Auris Health, Inc., ETHICON LLC, and Cilag GmbH International.

BACKGROUND

Field

The systems and methods disclosed herein are directed to surgical robotic control schemes.

Related Art

Surgical robotic systems can include a robotic arm for supporting and manipulating a medical instrument. The medical instrument can be mounted on a medical instrument driver of the robotic arm. The robotic arm can include a series of articulable joints connected by linkages. In certain implementations, the robotic arm can be manipulated by a surgeon via tele-operation to conduct a medical procedure using the robotic arm and medical instrument.

SUMMARY

According to one aspect of the disclosure, a surgical robotic system includes a robotic arm with a proximal end and a distal end. A plurality of linkages are coupled by a plurality of joints between the proximal and distal ends. One or more motors are coupled with at least one joint of the plurality of joints and configured to adjust a position of at least one linkage of the plurality of linkages. A sensor is coupled with the robotic arm. A memory with computer-executable instructions can cause a processor to: measure a force on the robotic arm with the sensor, the force located distal to the sensor, generate a signal based on the measured force, and control the one or more motors based on the signal to move the at least one linkage of the plurality of linkages.

According to another aspect, movement of the at least one linkage in response to the force is within a nullspace of the robotic arm without moving the medical instrument, the robotic arm includes a redundant degree of freedom for positioning the medical instrument.

According to another aspect, the redundant degree of freedom is along a support rail supporting the robotic arm.

According to another aspect, movement long the support rail is initiated by an input.

According to another aspect, movement of the at least one linkage in the nullspace is based on modelling a position of the at least one linkage in a virtual model of the robotic arm.

According to another aspect, a second robotic arm supports a second medical instrument. The computer-executable instructions are further configured to cause the processor to: measure a position of a second robotic arm, generate a second signal based on the positon of the second robotic, and control one or more motors of the second robotic arm based on the second signal to move a second linkage of the second robotic arm. The movement of the second linkage is within a nullspace of the second robotic arm without moving the second medical instrument. The second robotic arm includes a redundant degree of freedom for positioning the second medical instrument.

According to another aspect, generating the second signal is further based on the robotic arm being within a trigger distance of the second robotic arm.

According to another aspect, the computer-executable instructions are further configured to cause the processor to: increase a resistance of the at least one joint to movement in a first direction based on a proximity of the robotic arm to an adjacent structure.

According to another aspect, the robotic arm includes an input configured to be activated by a user. The memory further includes computer-executable instructions to cause the processor to: receive a user input signal generated by activation of the input by the user and control the one or more motors to move the at least one linkage further in response to receiving the user input signal.

According to another aspect, the input is a button on the robotic arm.

According to another aspect, the input is on the distal portion of the robotic arm.

According to another aspect, the input is a donut button on the instrument drive mechanism.

According to another aspect, the robotic arm further includes a cannula detection sensor configured to detect a docked/undocked state of the robotic arm to a cannula. The memory further includes computer-executable instructions to cause the processor to: receive a cannula input signal from the cannula detection sensor, and control the one or more motors to move the at least one linkage further in response to receiving the cannula input signal and the measured force on the robotic arm.

According to another aspect, the memory further comprises computer-executable instructions to cause the processor to: compare the force measured with the sensor to a threshold force, and control the one or more motors to move the at least one linkage further in response to the force being above the threshold force.

According to another aspect, the sensor is a load cell.

According to another aspect, the sensor is a six degree of freedom load cell bridging a structural break in the linkage and the threshold force is based, at least in part, on a mass of the robotic arm and forces of gravity.

According to another aspect, the sensor is a force sensor.

According to another aspect, the sensor is a load cell are coupled with a grab point on the distal portion of the robotic arm.

According to another aspect, the distal portion of the robotic arm further comprises an instrument drive mechanism configured to couple with a medical instrument.

According to another aspect, the force is configured to adjust alignment of the medical instrument.

According to another aspect, movement of the at least one linkage adjusts a position of a remote center of motion of the medical instrument.

According to another aspect, controlling the one or more motors to move the at least one linkage further includes controlling at least two of the plurality of joints to move in a first direction.

According to another aspect, the robotic arm is further configured to operate tele-operatively.

According to one aspect of the disclosure, a surgical robotic system includes a robotic arm with a proximal portion and a distal portion. The distal portion includes an instrument drive mechanism configured to drive a medical instrument attached thereto. A plurality of linkages are coupled together by a plurality of independently actuatable joints between the proximal portion and the distal portion thereby accommodating movement of the medical instrument in multiple degrees of freedom. At least one of the degrees of freedom is redundant to a position of the medical instrument. An arm support is coupled with the proximal portion of the robotic arm. An input is configured to be activated by a user. A memory storing computer-executable instructions to cause a processor to: detect activation of the input, generate a user input signal based on detecting activation of the input, and control, based on receiving the user input signal, at least one joint of the plurality of joints to allow movement of at least one linkage of the plurality of linkages in a first direction without moving the medical instrument.

According to another aspect, the robotic arm is further configured to operate tele-operatively.

According to another aspect, the proximal portion of the arm support comprises a rail and a linear joint configured to translate the at least one linkage along the rail in the first direction.

According to another aspect, robotic arm includes a force sensor and the computer-executable instructions further configured to cause the processor to: measure a force on the robotic arm with the sensor, generate a signal based on the measured force, and control a motor of the linear joint to move the at least one linkage along the rail in the first direction.

According to one aspect of the disclosure, a surgical robotic system includes a robotic arm with a proximal portion and a distal portion. The distal portion includes an instrument drive mechanism configured to drive a medical instrument attached thereto. A plurality of linkages are coupled together by a plurality of independently actuatable joints between the proximal portion and the distal portion thereby accommodating movement of the medical instrument in multiple degrees of freedom. At least one of the degrees of freedom is redundant to a position of the medical instrument. An arm support are coupled with the proximal portion of the robotic arm. A force sensor is on the proximal portion of the robotic arm. A processor and a memory storing computer-executable instructions cause the processor to: measure a force on the robotic arm with the force sensor, the force distal to the force sensor along the robotic arm, generate a control signal based on the force, and control, based on the control signal, at least one joint of the plurality of joints to allow movement of at least one linkage of the plurality of linkages without moving the medical instrument.

According to another aspect, the robotic arm is further configured to operate tele-operatively.

According to another aspect, generating the control signal is further based on the force being above a threshold.

According to another aspect, the force is from contact with an adjacent structure during tele-operation of the robotic arm.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
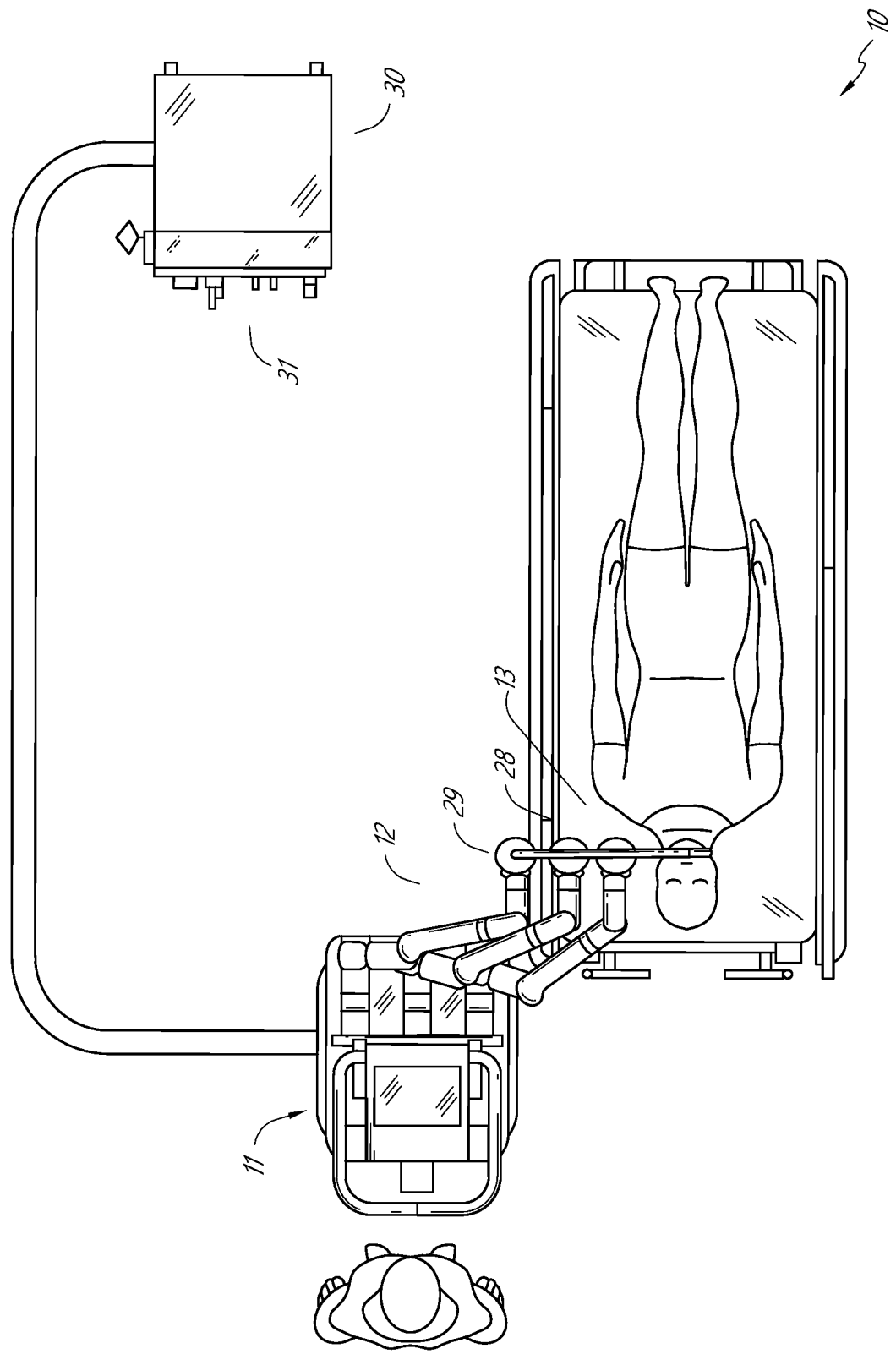
FIG. 1 illustrates an embodiment of a cart-based robotic system arranged for diagnostic and/or therapeutic bronchoscopy.
Figure 2:
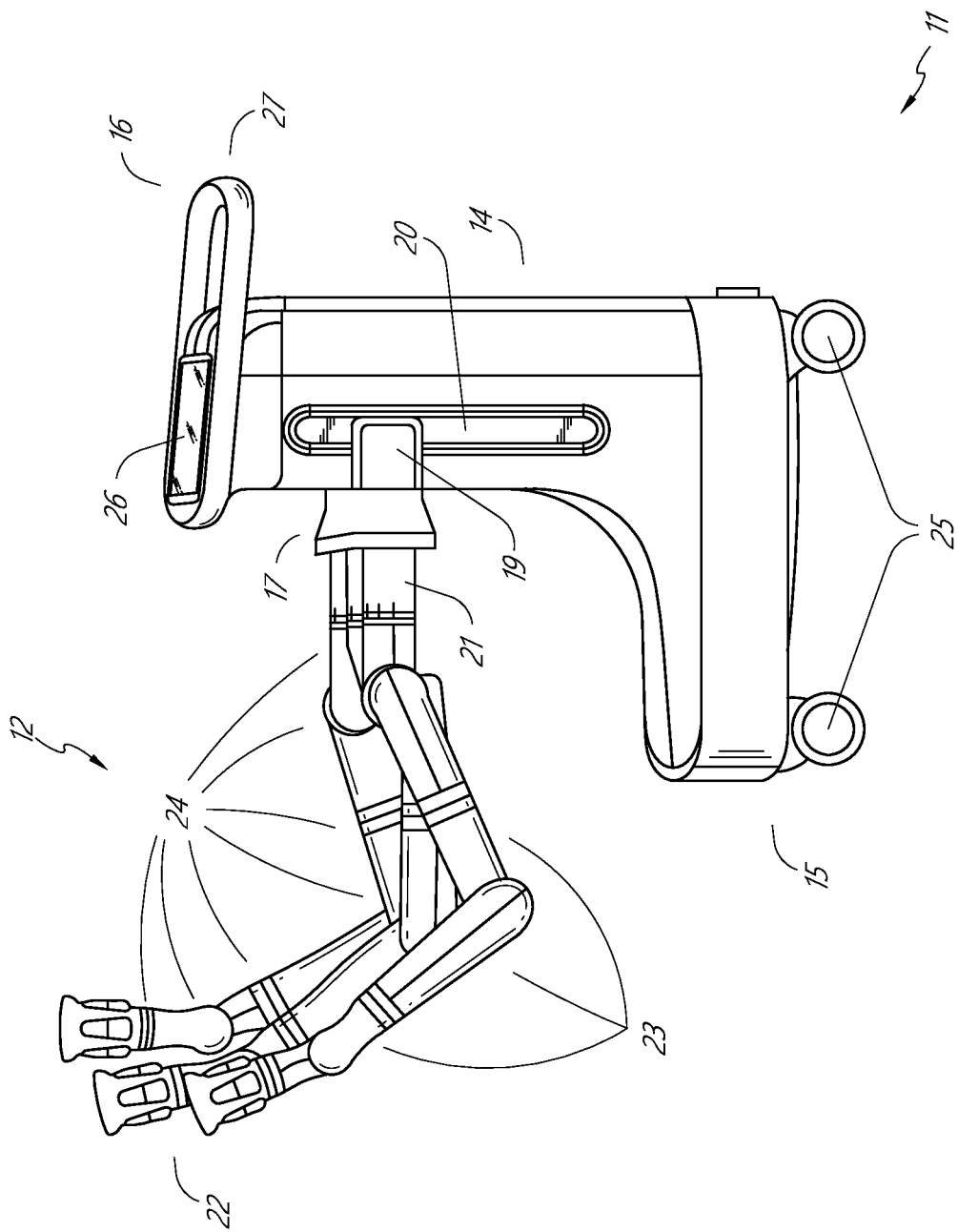
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
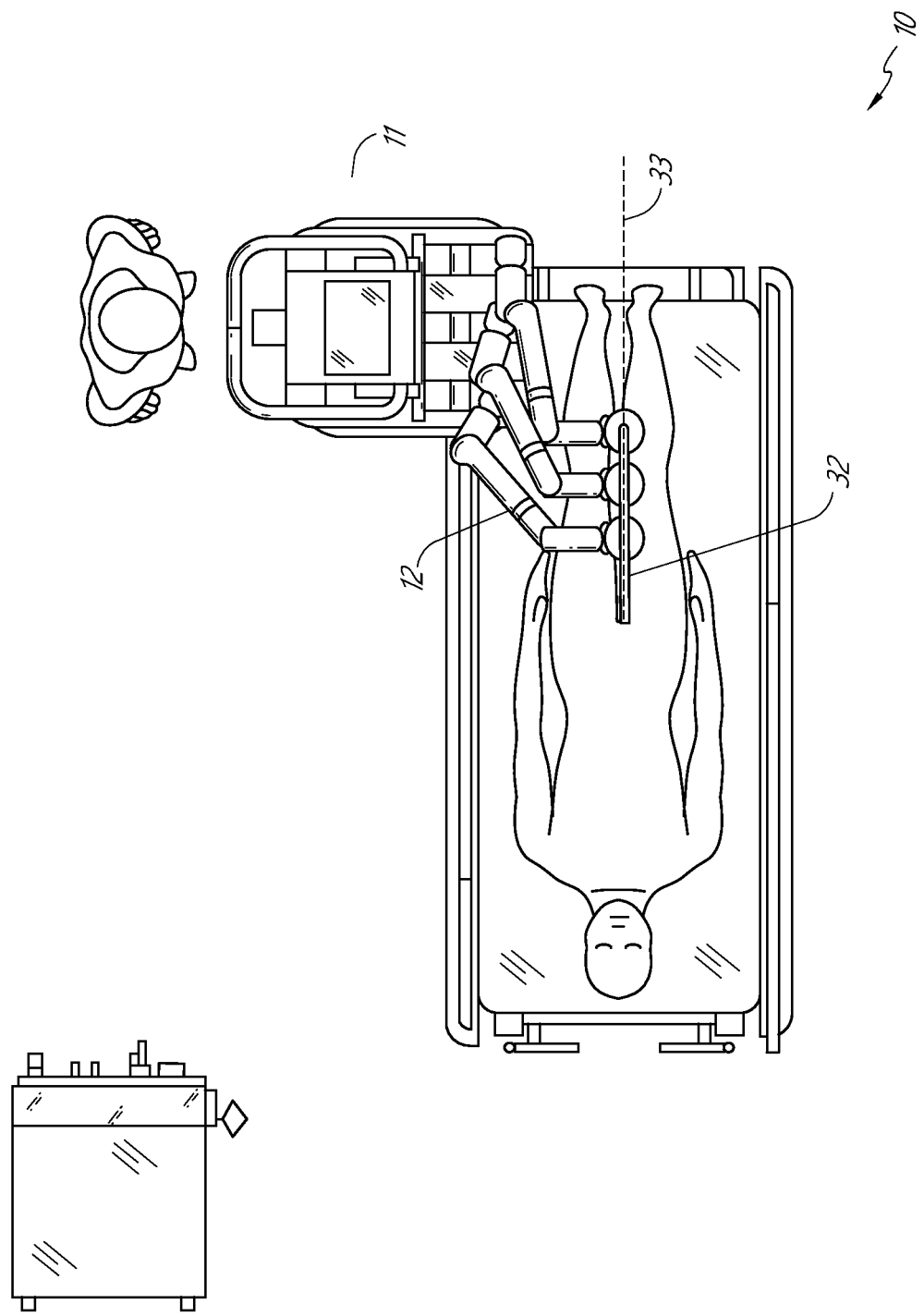
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
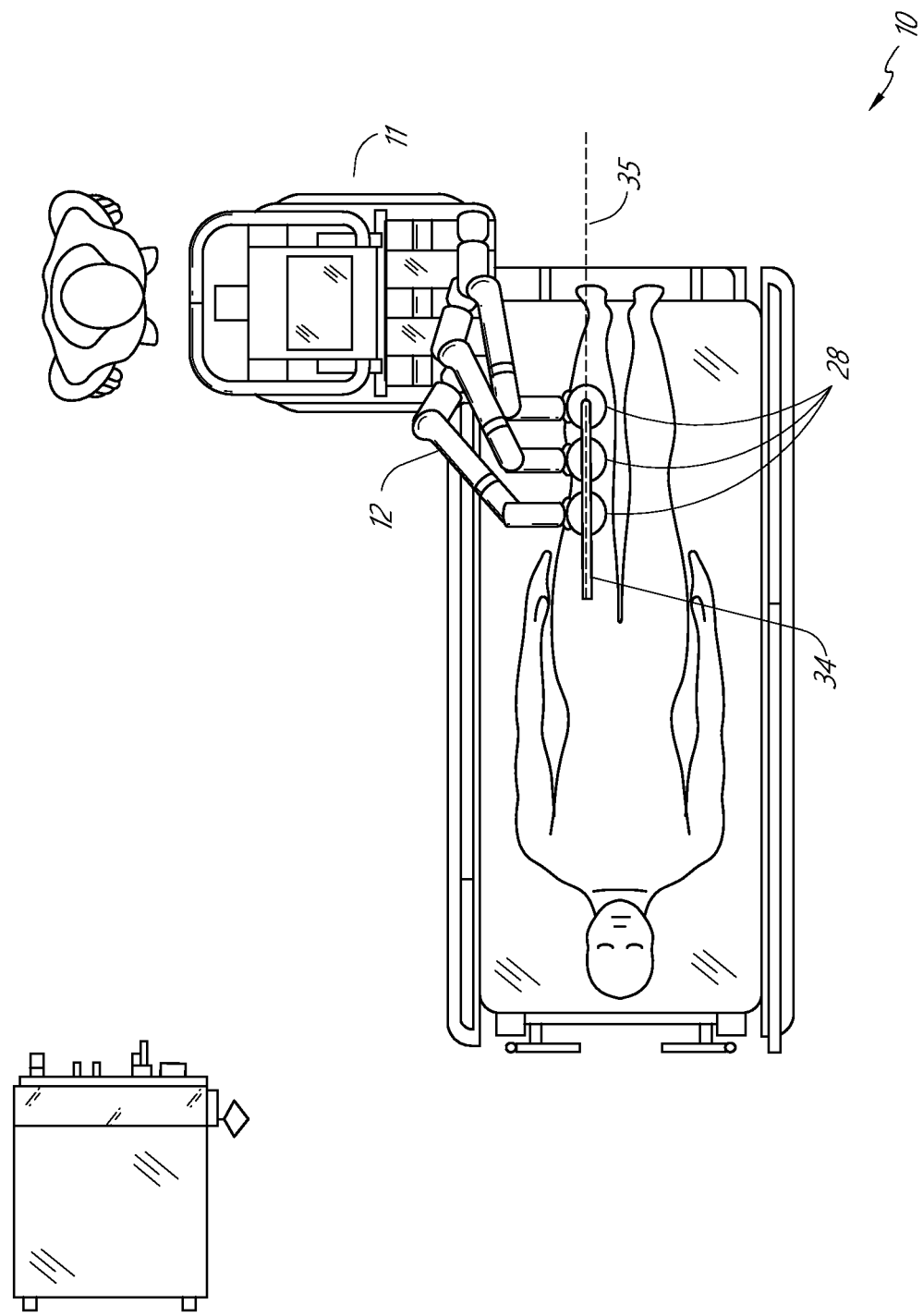
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
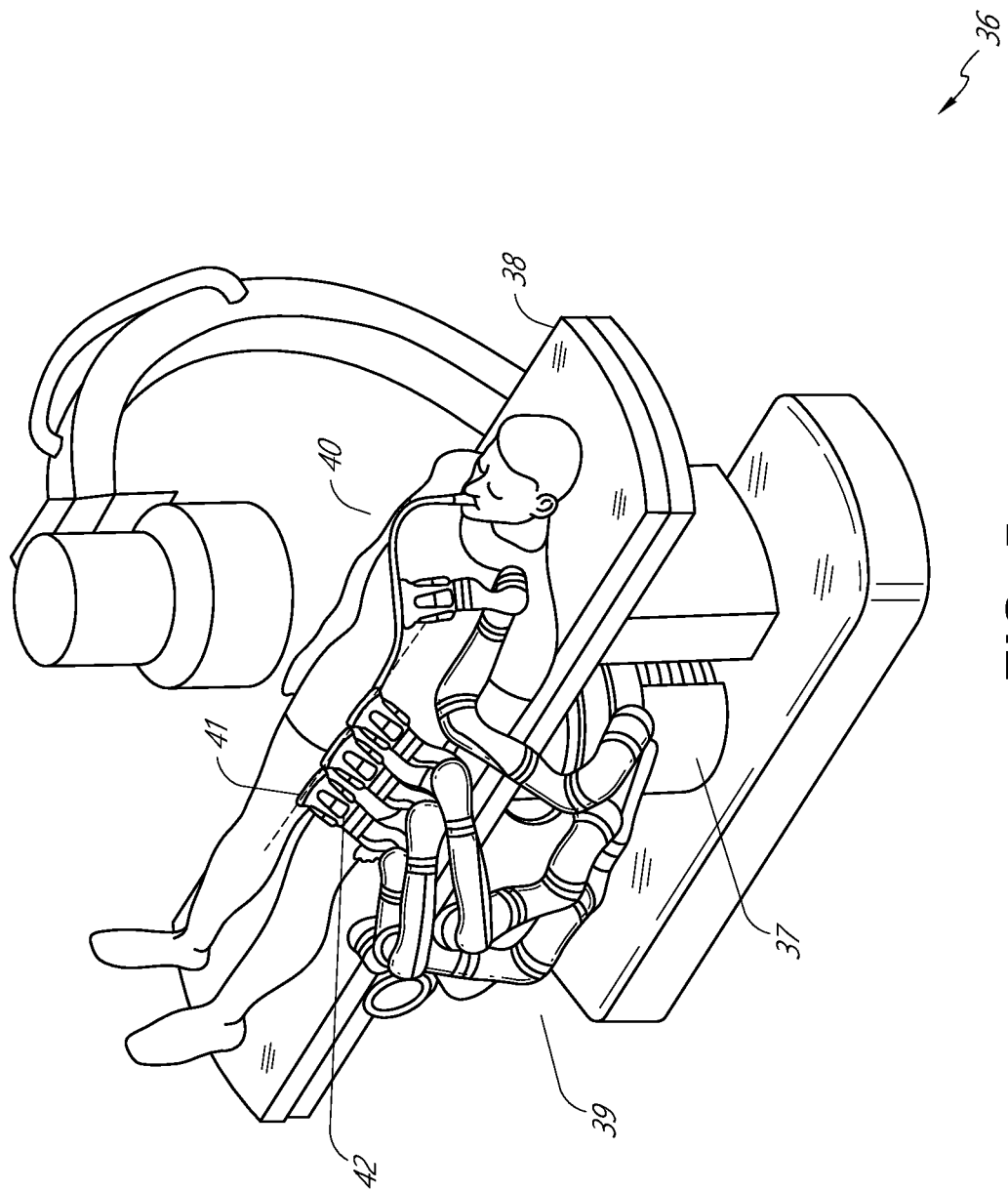
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
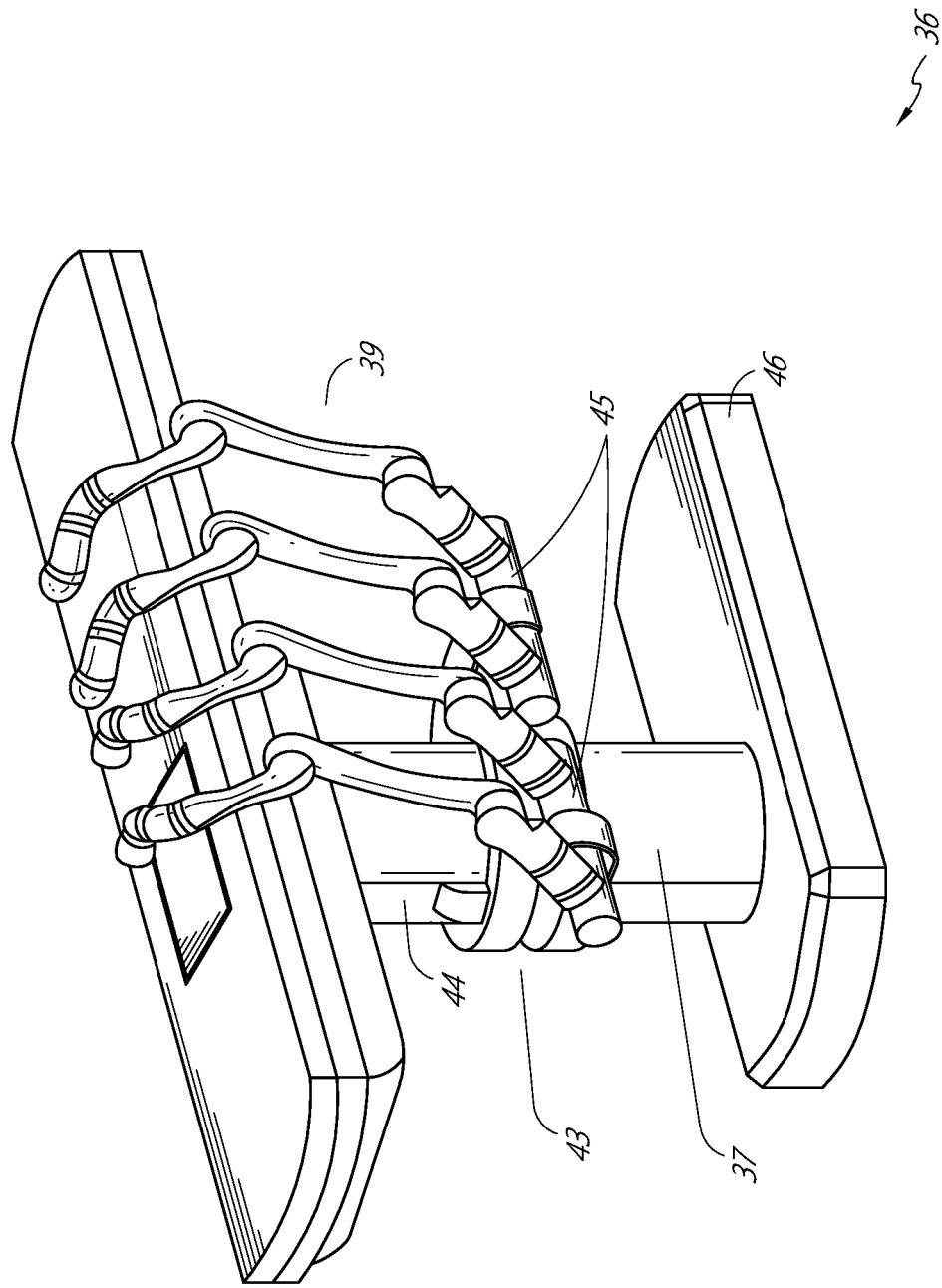
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
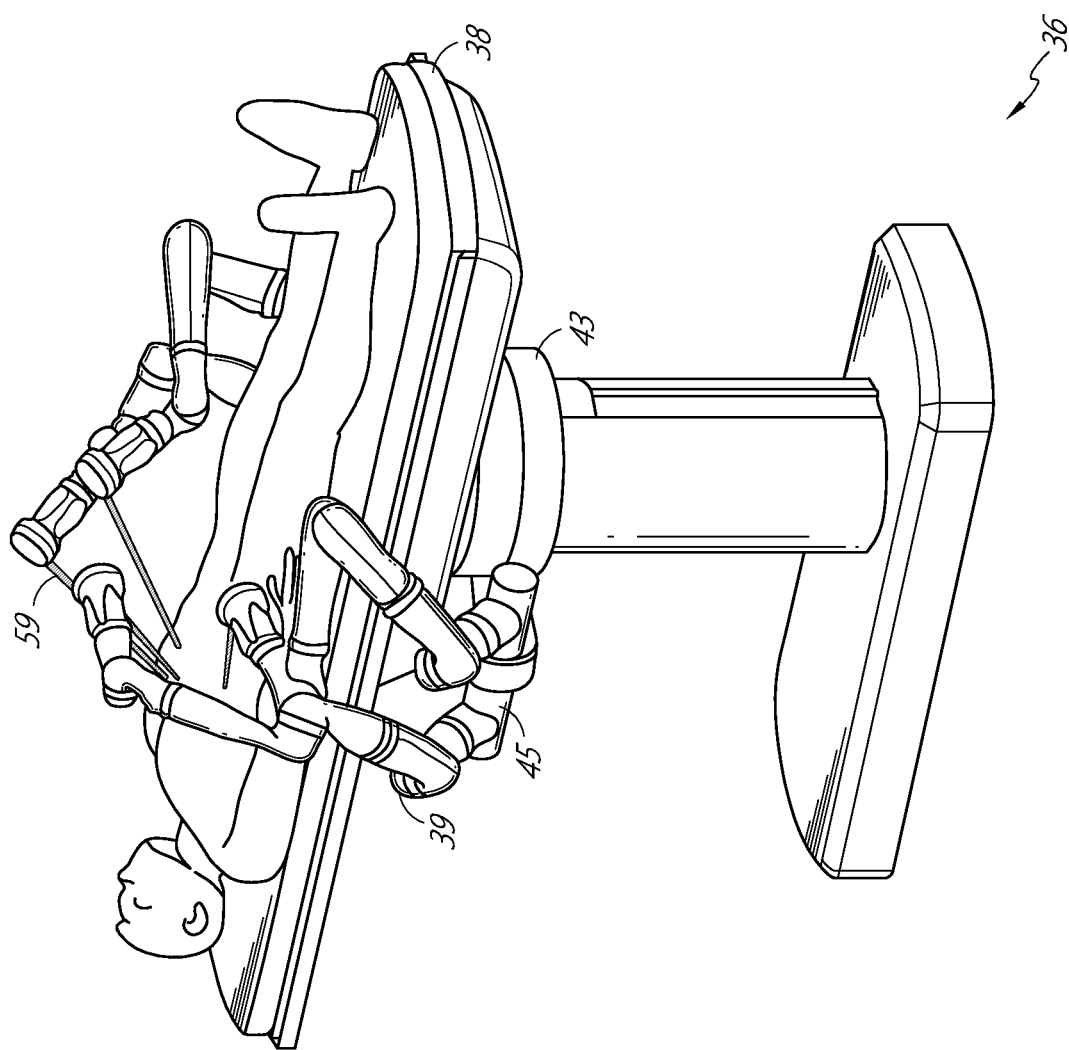
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
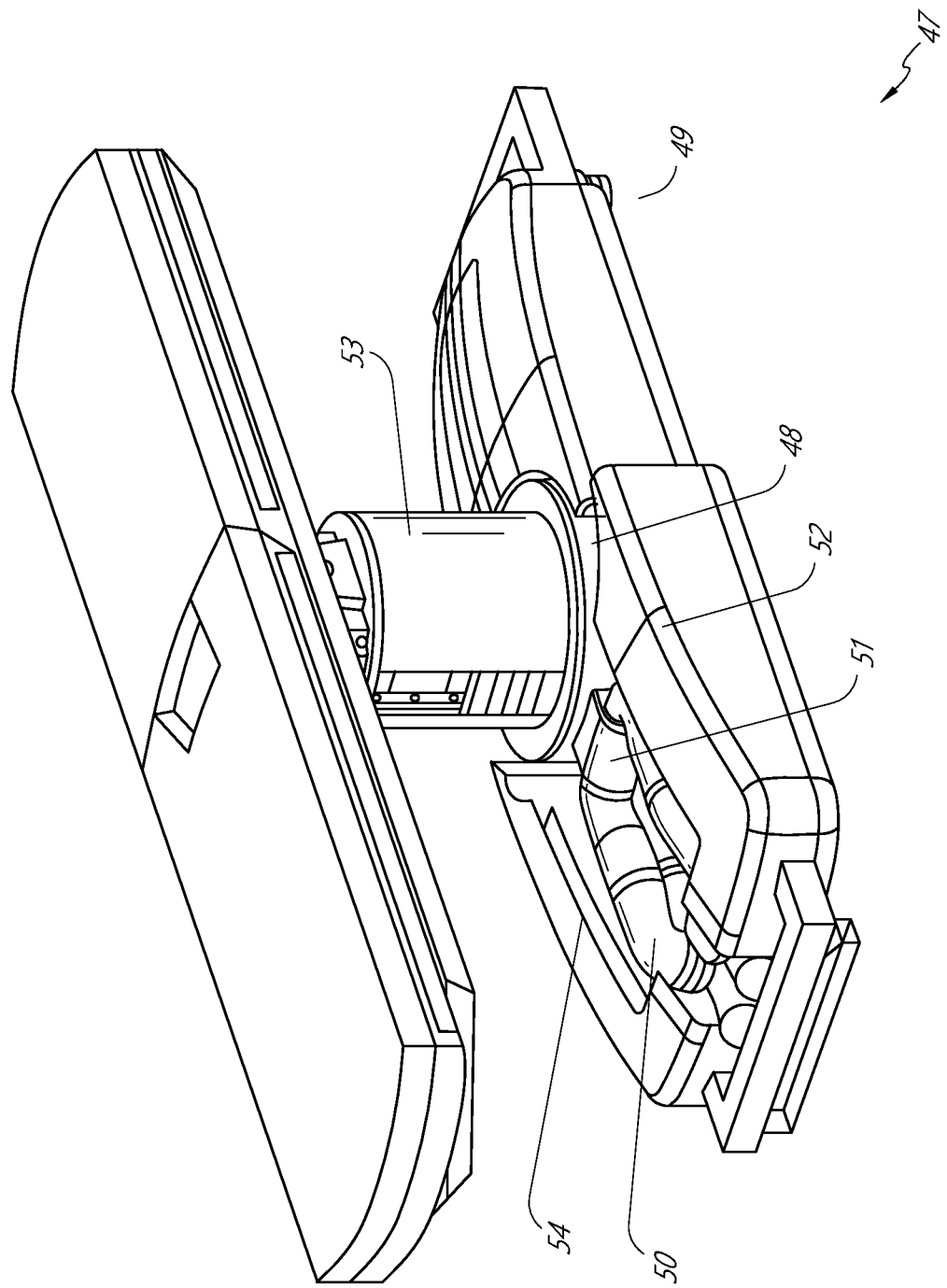
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
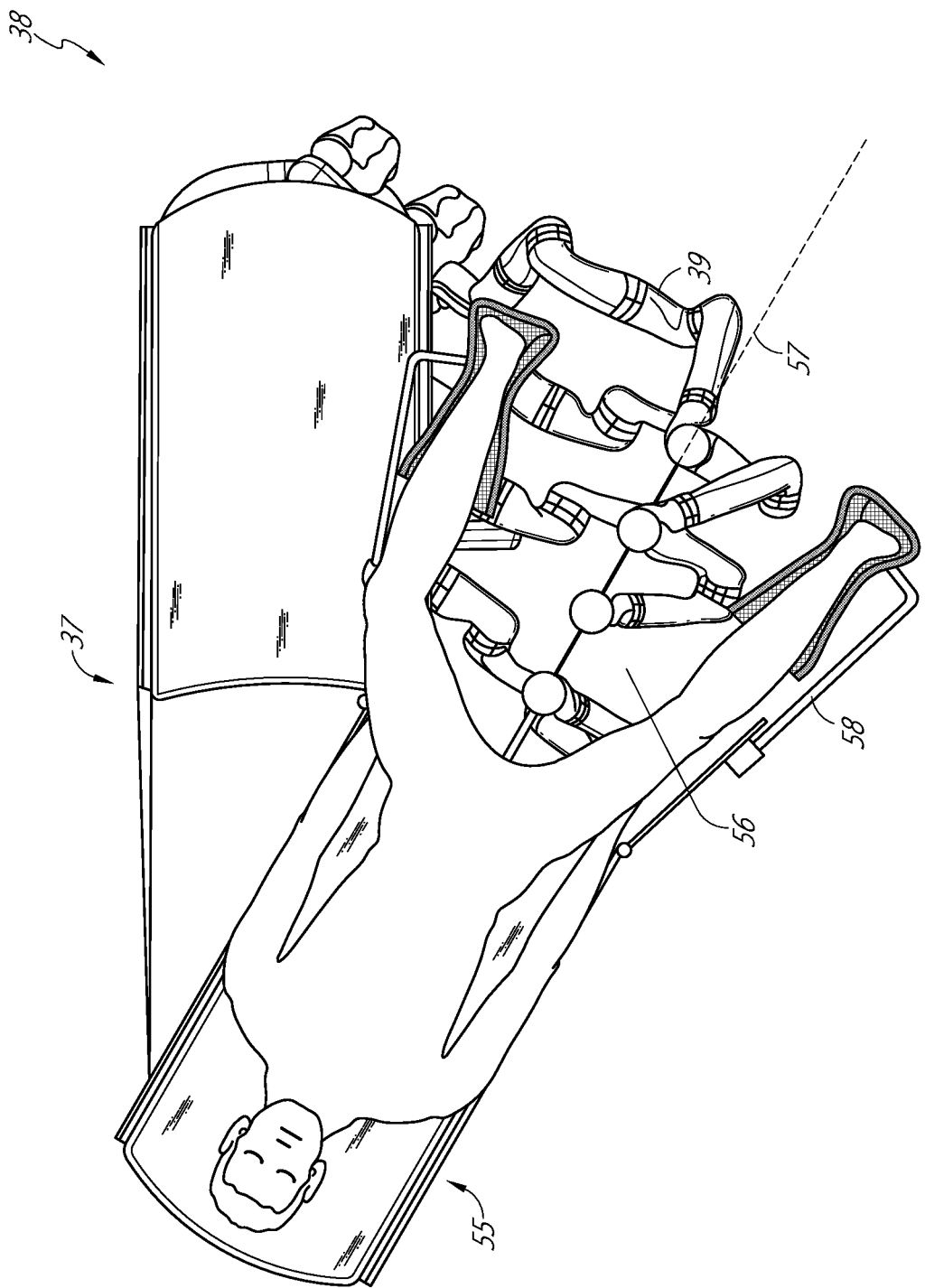
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
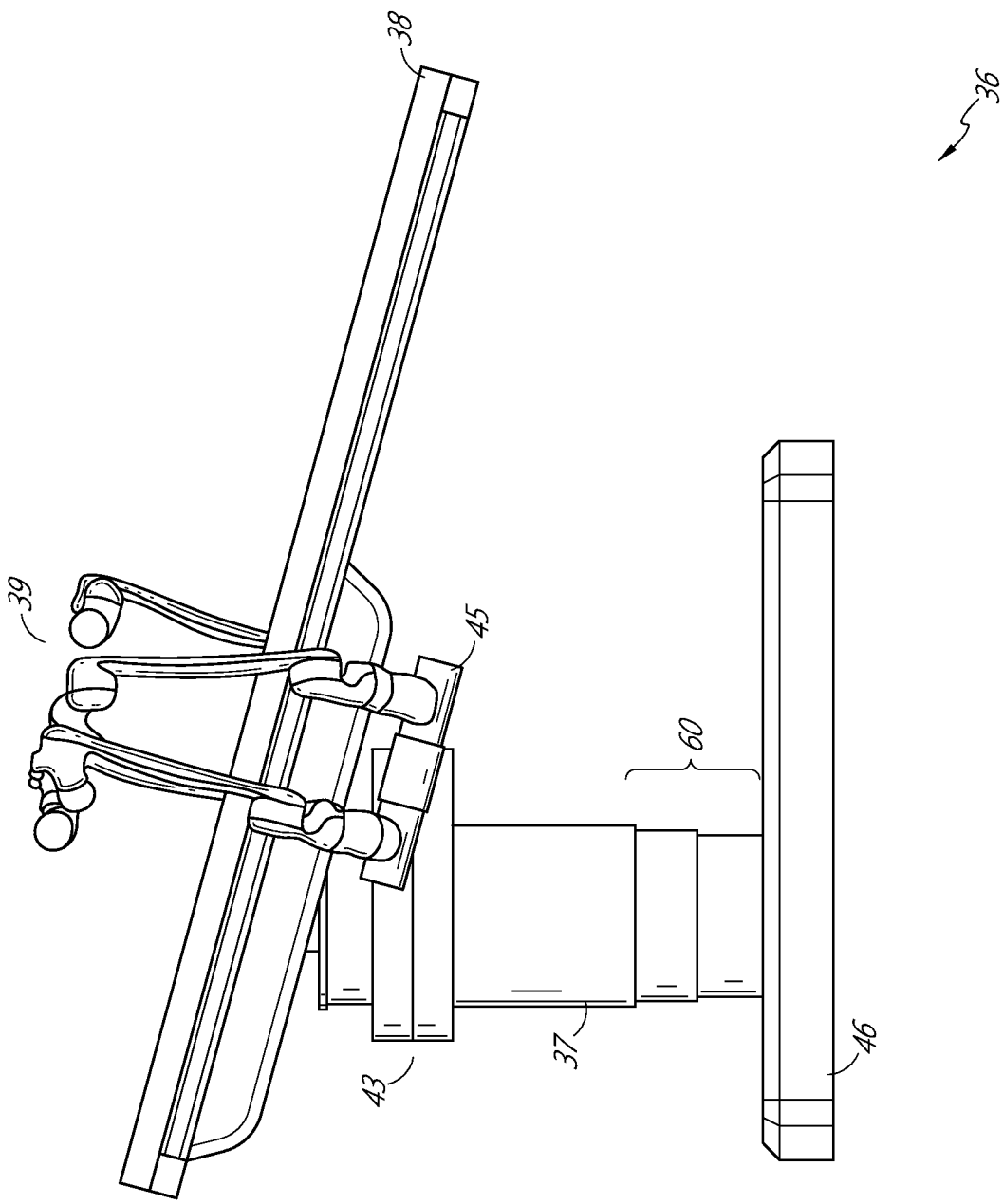
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
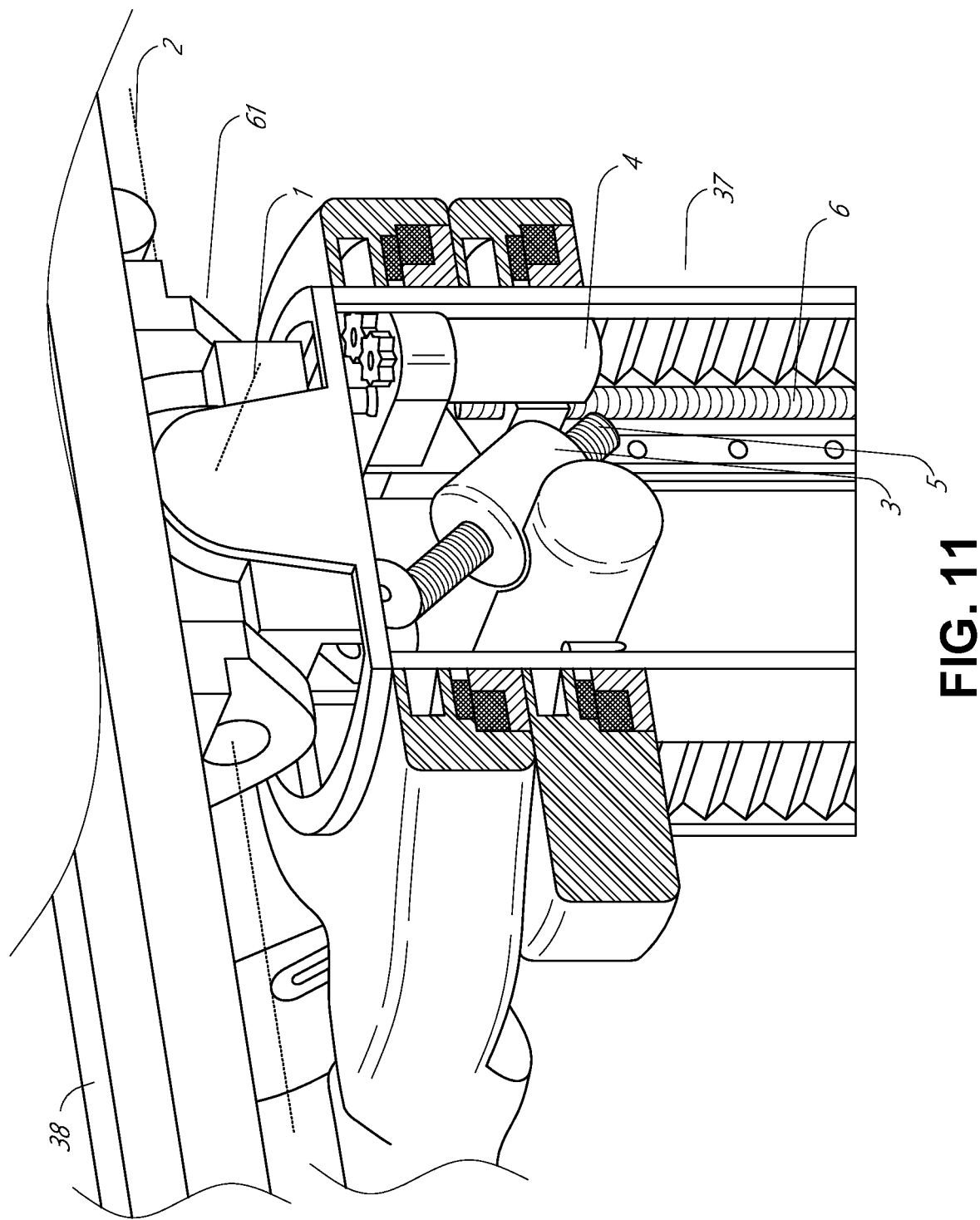
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
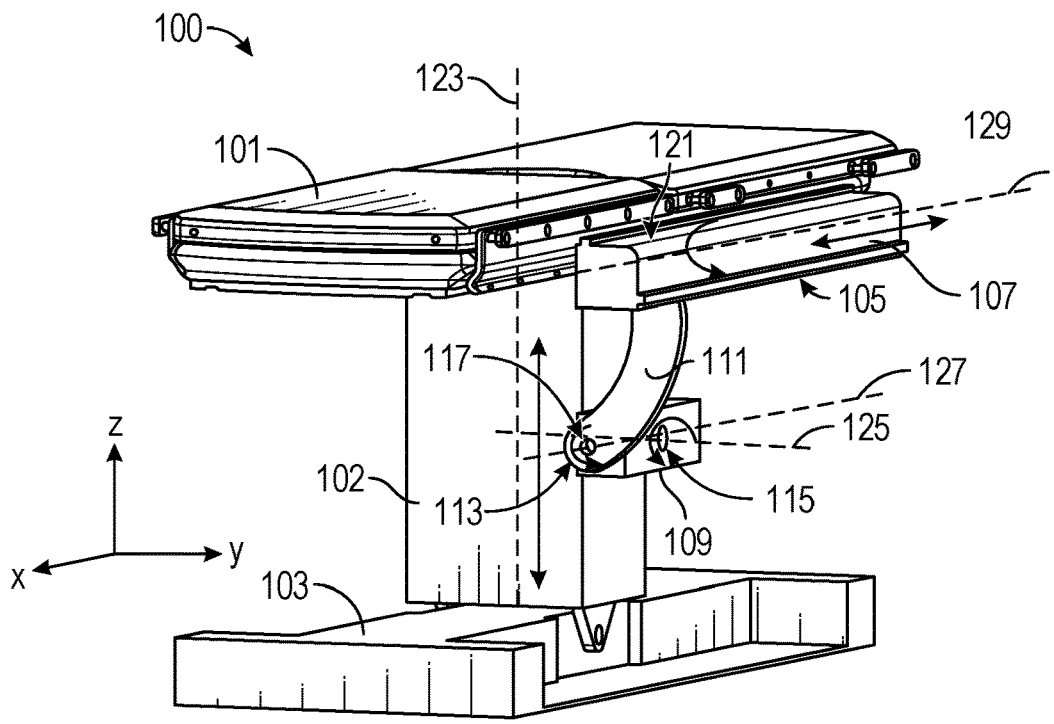
FIG. 12 illustrates an alternative embodiment of a table-based robotic system.
Figure 13:
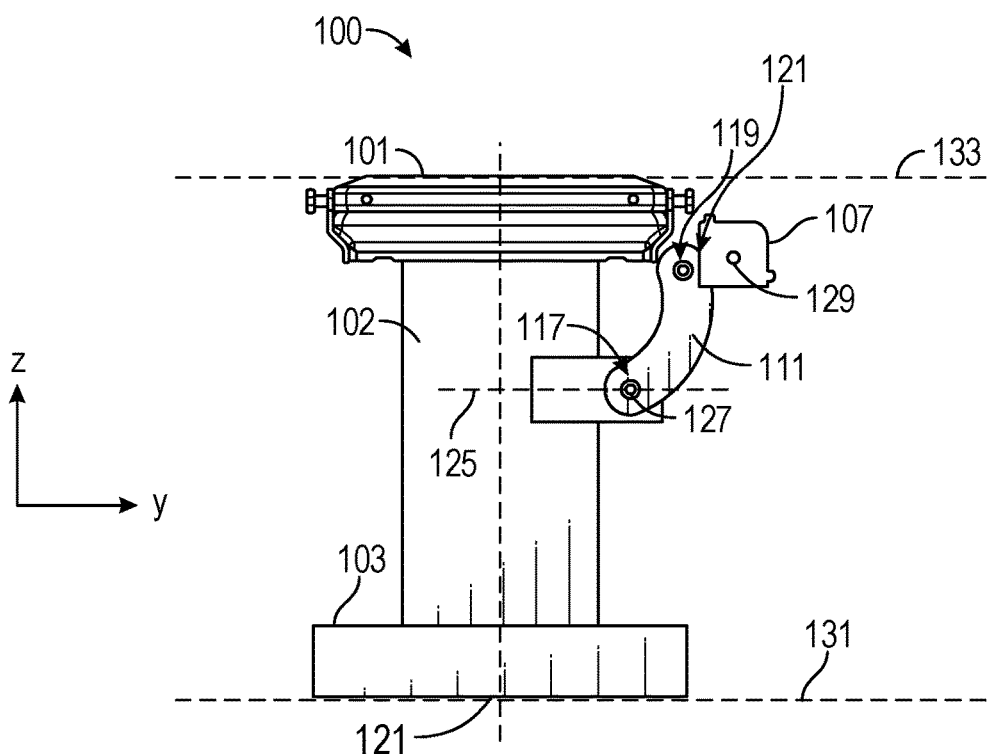
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc.

In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
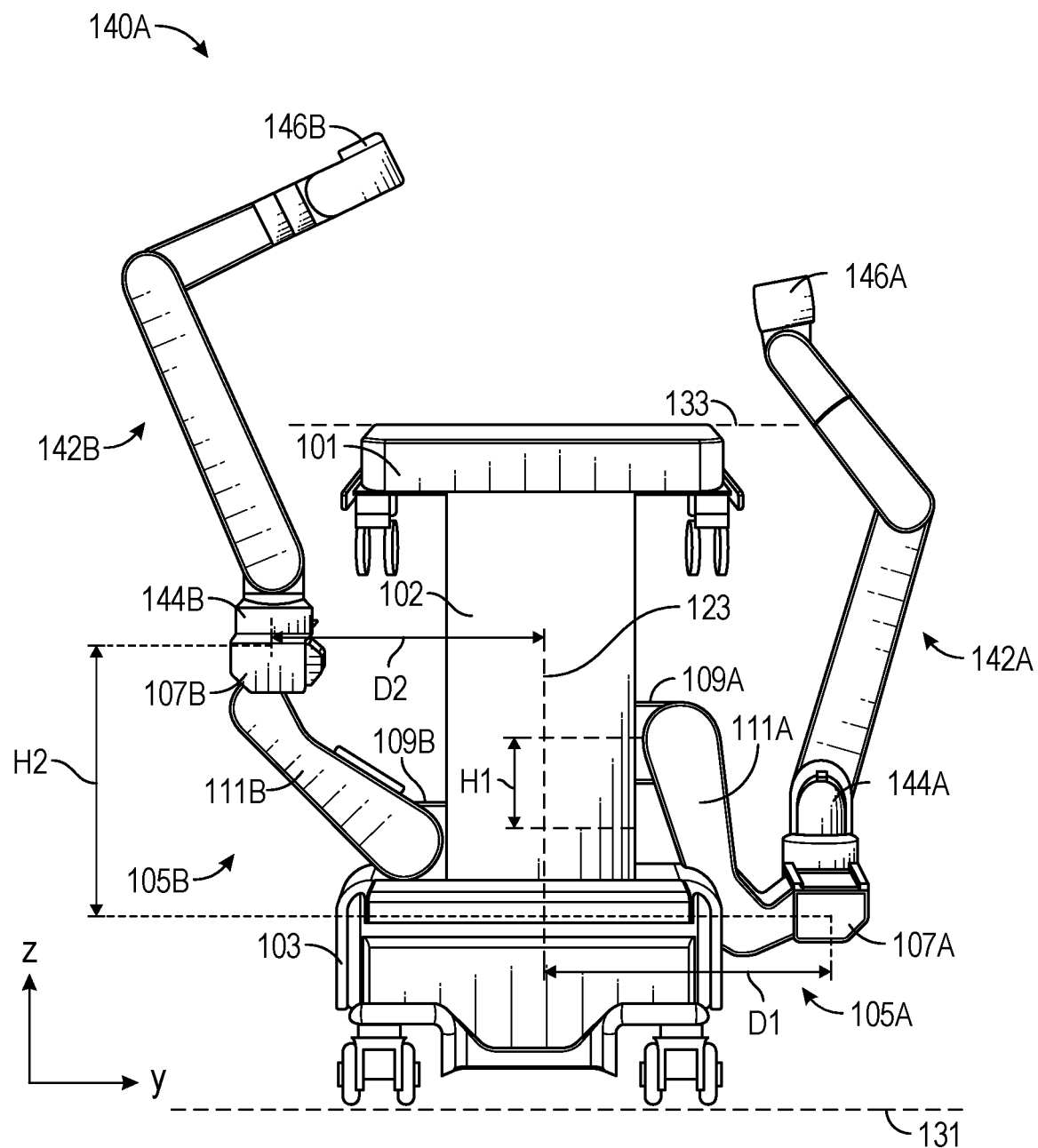
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
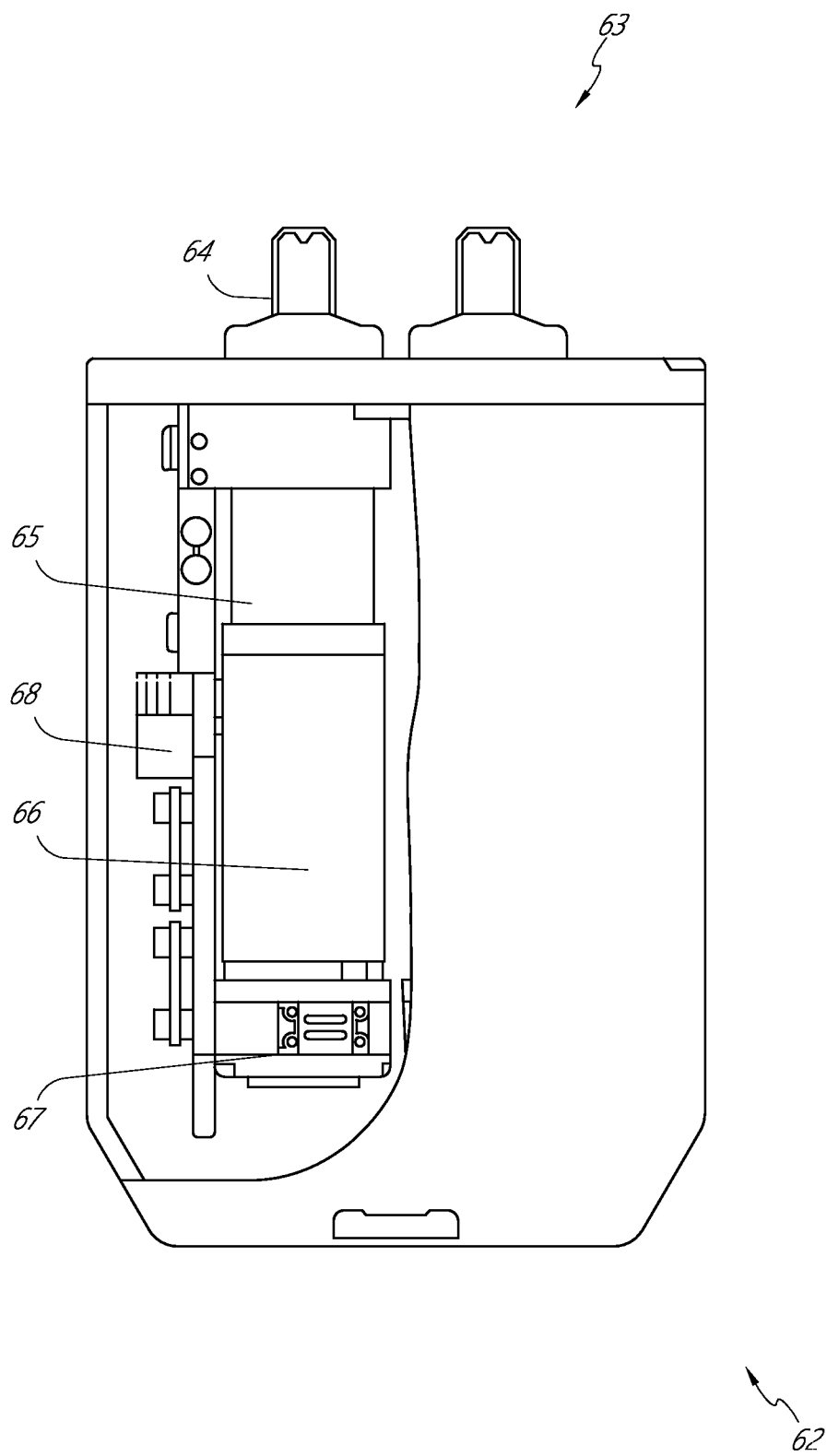
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
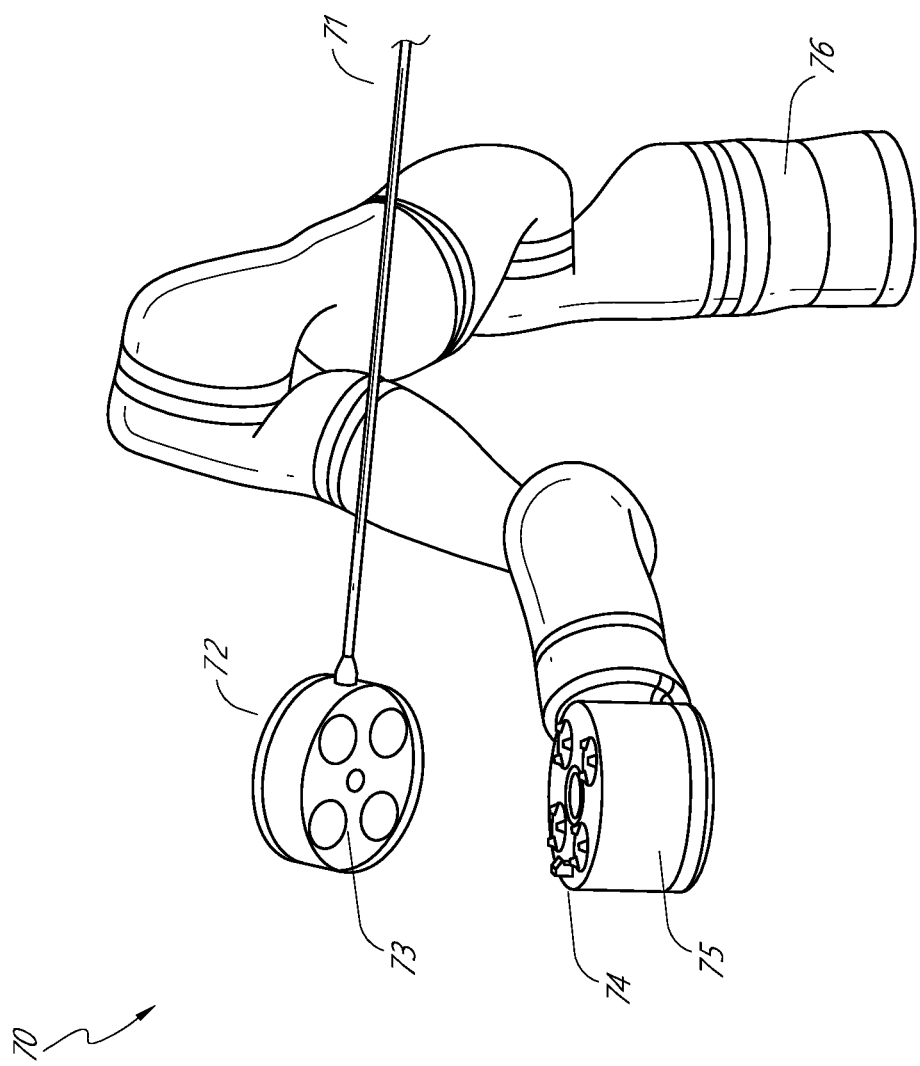
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
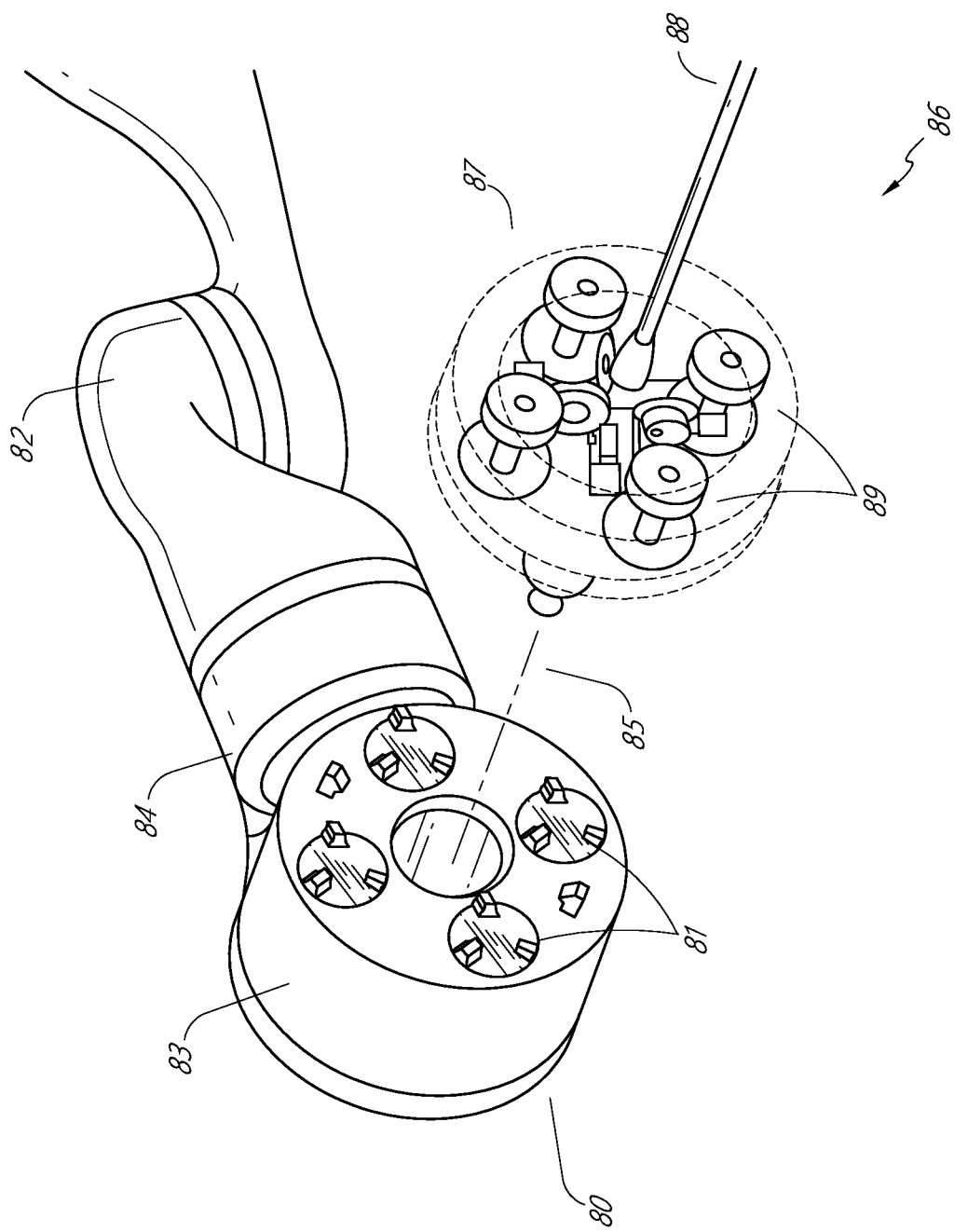
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
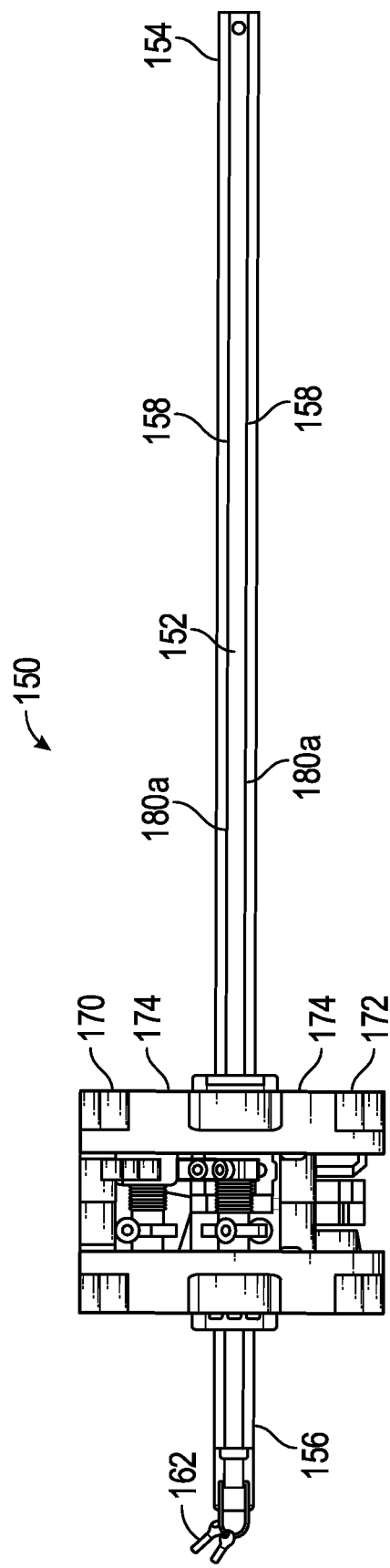
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
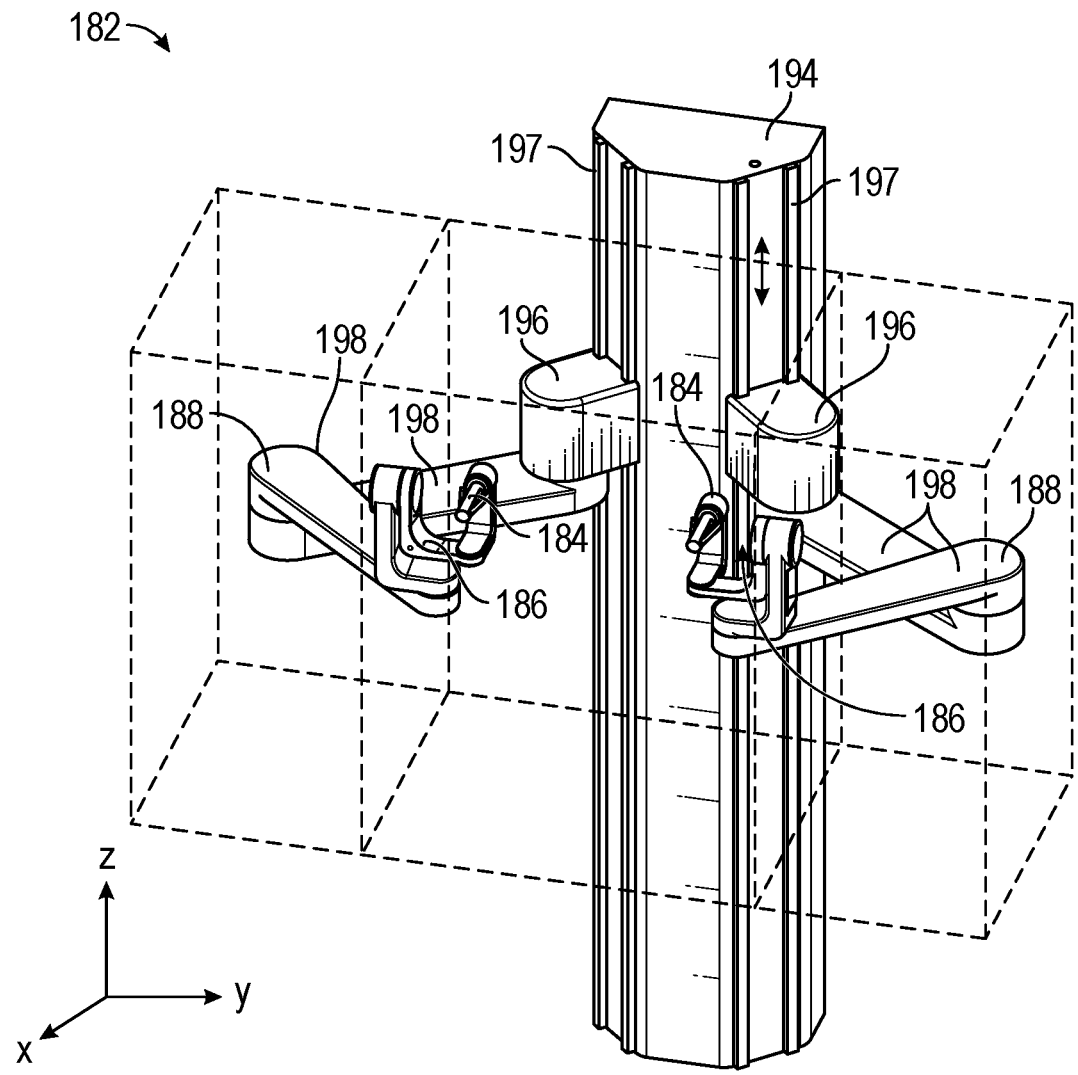
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
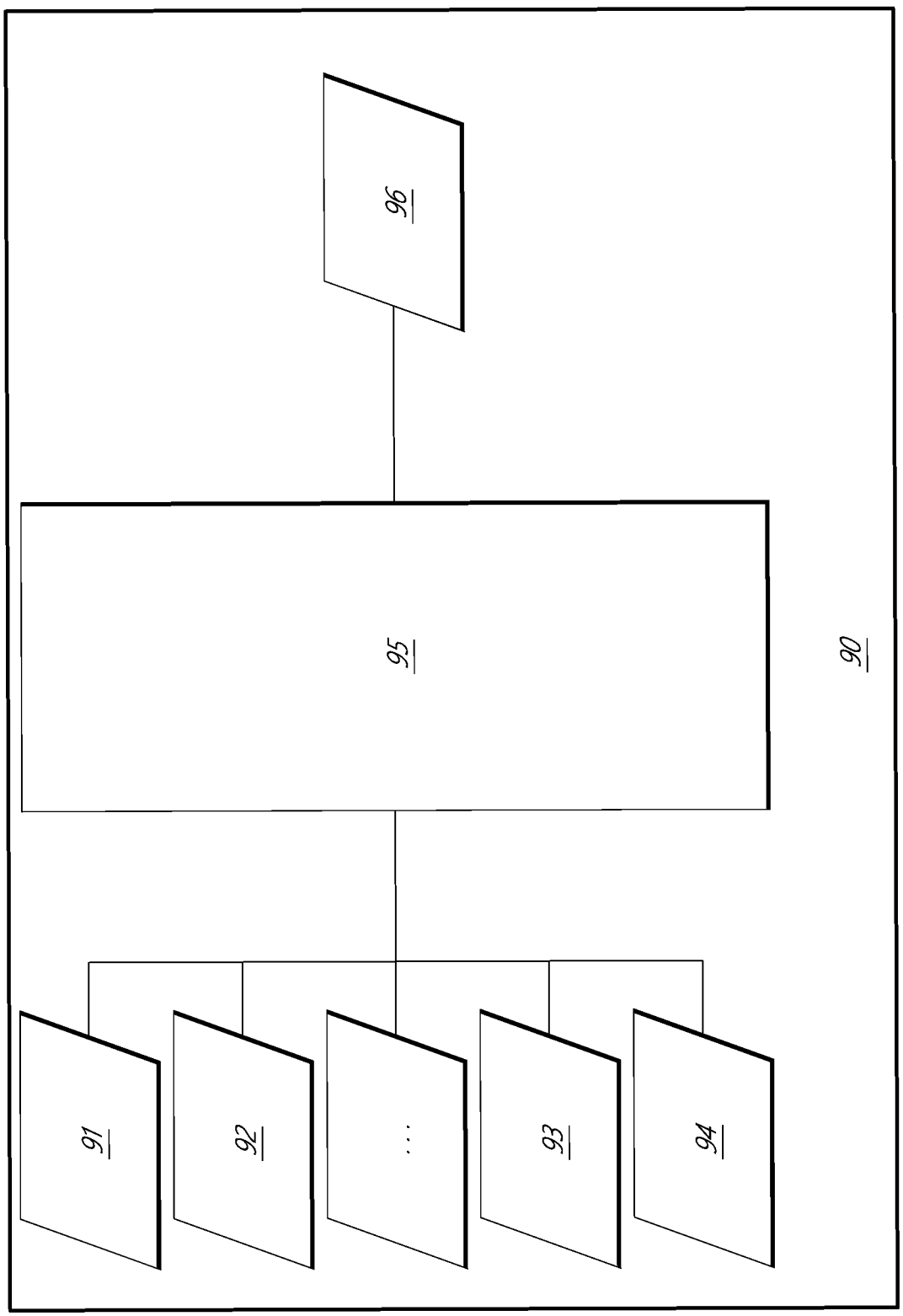
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Surgical Robot Systems and Control Schemes

Surgical robotic systems (such as the surgical systems shown and described in relation to FIGS. 1-20) generally include multiple robotic arms or manipulators for performing different types of medical (e.g., surgical) procedures. The robotic arms can be controlled by a clinician tele-operatively, or by an assistant directly (e.g., via manual manipulation). These functions may be provided separately or simultaneously based on workflow needs. Each of the robotic arms can move via one or more control schemes, which are the subject of this disclosure. The integration of these control schemes with sensor architecture can facilitate proper control, mode combination, and switching to smoothly align with medical procedure workflow needs.

A. Surgical Robotic Systems

Figure 21A:
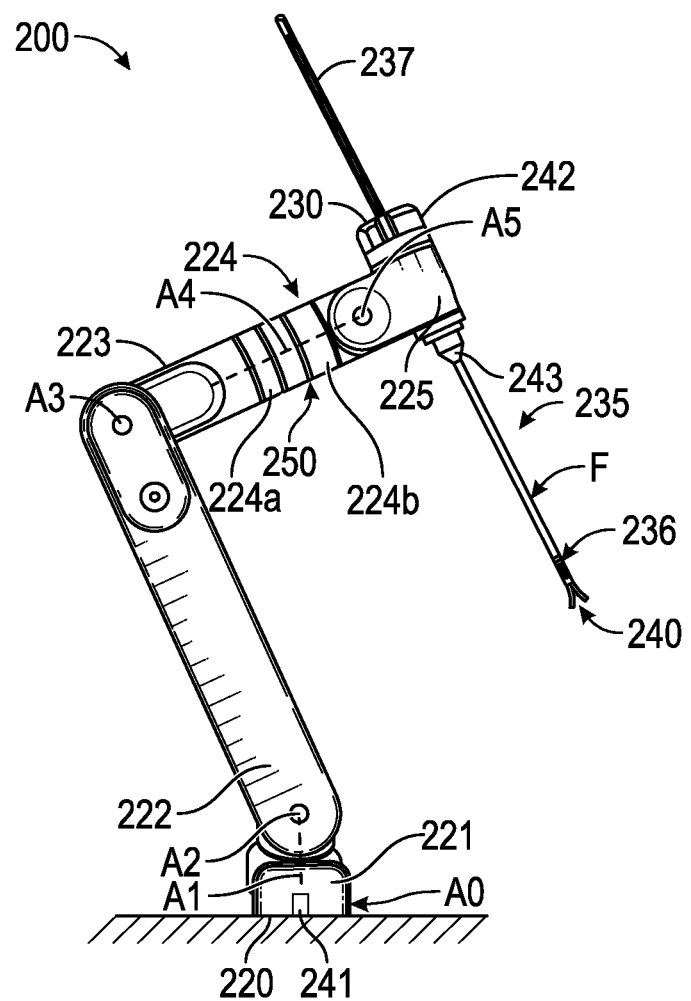
FIG. 21A shows an example of a robotic arm including a load cell.
Figure 21B:
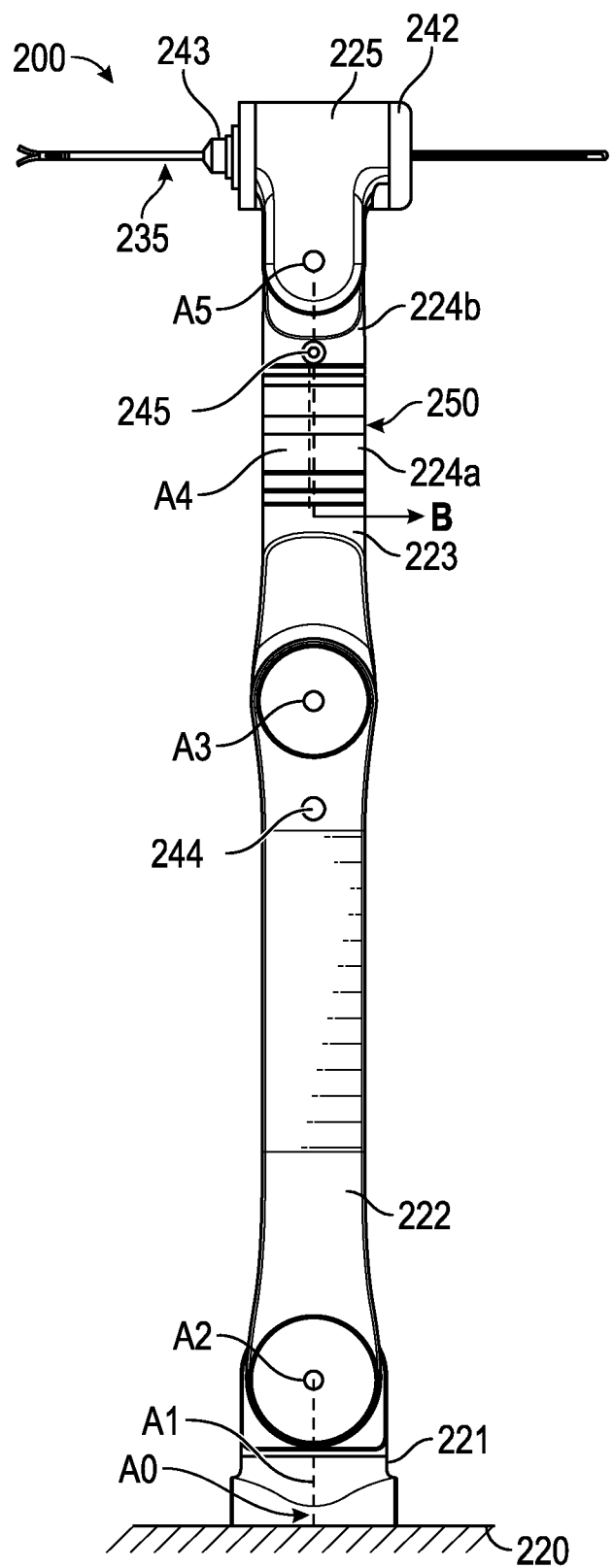
FIG. 21B shows a front view of the robotic arm in FIG. 21A.

FIGS. 21A-B shows an example of a robotic arm 200, which can be a component of a robotic surgical system according to the present disclosure. The robotic arm 200 can include a series of linkages 221, 222, 223, 224, and/or 225 connected by independently articulable joints. The series of linkages can be mounted on a support rail 220. The independently articulable joints can include representative joints A0, A1, A2, A3, A4 and/or A5. The joints A1-A5 can variously include rotation joints. Each joint can include a motor and/or a controller (e.g., servo-controller). The third joint A3 can be an elbow joint. The fourth and fifth joints A4, A5 can form a wrist joint of the robotic arm 200. The fourth joint A4 can be a roll joint and the fifth joint A5 can be a pitch joint. The A0 joint can allow linear translation along the support rail 220. The first link 221 can be translatable along the support rail 220 through the A0 joint. The robotic arm 200 can have six or more degrees of freedom. In certain implementations, the robotic arm 200 can include at least one excess degree of freedom for a given position of a distal end of the robotic arm.

The robotic arm 200 can include a medical instrument driver 230 (e.g., instrument driver 75). The medical instrument driver 230 can be located on a distal end of the robotic arm 200 (e.g., on the fifth link 225). The medical instrument driver 230 can be removably coupled with a medical instrument 235. The medical instrument 235 can include an elongate shaft. The elongate shaft can extend from a first end 236 to a second end 237. The first end 236 can include an end effector 240. The end effector 240 can be any of various medical instruments such as but not limited to grippers, lances, probes, endoscopes, shears or other surgical tools.

The medical instrument 235 can be operable via the medical instrument driver 230. The medical instrument 235 can be positionable via the articulable joints of the robotic arm 200. The articulable joints and/or the medical instrument driver 230 can be controlled in response to user inputs via tele-operation through a controller (e.g., using the controller 182). A clinician can also manually manipulate the robotic arm 200 to position the articulable joints and/or the medical instrument 235. The response of the robotic arm 200 to the manual manipulation can depend on the operating control scheme of the robotic arm 200, as described further below.

The robotic arm 200 can include a multi-axis load cell 250. The load cell 250 can be positioned between a proximal portion 224a and distal portion 224b of the robotic arm. In one implementation, the load cell 250 can bridge a structural break in the fourth linkage 224 (or any other linkage) of the robotic arm. The load cell 250 can structurally support the distal portion 224b of the robotic arm 200, including the medical instrument driver 230 and/or medical instrument 235. The multi-axis load cell 250 can be a 6-axis load cell (measuring forces and moments about the x, y, and z-directions). In another implementation, the multi-axis load cell 250 is a 3-axis load cell. In another embodiment, the load cell 250 can be distributed joint sensor (e.g., for the system 10).

The multi-axis load cell 250 can detect and/or measure a force F acting on the distal portion 224b, such as on the medical instrument 235 or the medical instrument driver 230. In some embodiments, the load cell 250 can be used as an input for an admittance control scheme for manual manipulation of the robotic arm 200. The load cell 250 can also detect potential overloading of the articulable joints of the robotic arm 200 or other components of the robotic arm 200.

The A0 joint can include a force sensor 241. The force sensor 241 can be located at or near the A0 base joint (e.g., at the connection with the support rail 220). The force sensor 241 can detect and/or measure the force F on the robotic arm 200. The force F can be distal to the force sensor 241. The force sensor 241 can detect components of the force F acting along a direction of travel of the robotic arm 200 along the support rail 220. The force sensor 241 can be used as a switch to enter a nullspace jogging control scheme for manually adjusting the robotic arm 200, as described further below.

The robotic arm 200 can include a cannula detection sensor 243. The cannula detection sensor 243 can be a magnetic, mechanical, pressure, optical, or other sensor type. The cannula detection sensor 243 can detect the docked or undocked state of the robotic arm 200 with a cannula (e.g., connected with a patient and configured to receive the medical instrument 235). The control scheme of the robotic arm 200 or the control schemes available to the robotic arm 200 can be based on the docked or undocked state of the robotic arm 200, as detected by the cannula detection sensor 243.

The robotic arm 200 can include a button 242. The button 242 can be positioned on or near the medical instrument driver 230. The button 242 can be a donut-shaped button. The button 242 can be positioned around the second end 237 of the elongate shaft of the medical instrument 235. The button 242 can be actuated once, held, or actuated in a pattern (e.g., three clicks). The button 242 can be actuatable by a clinician to alter or select a control scheme of the robotic arm 200. For example, pressing the button 242 can toggle activation of the admittance control scheme whereby the 6-axis load cell 250 can be used to detect forces applied to the robotic arm 200.

In addition to the button 242, the robotic arm can also include other inputs or touchpoints. Actuating the different input buttons this can place the robotic arm in different types of control modes, as described below. The robotic arm 200 can include a proximal link button 244. The proximal link button 244 can be positioned on the second link 222 or adjacent to the elbow joint of robotic arm 200. The proximal link button 244 can be used to alter or select the control scheme of the robotic arm 200.

The robotic arm 200 can include a distal link button 245. The distal link button 245 can be positioned on the fourth link 224 or the fifth link 225 (e.g., adjacent to the medical instrument driver 230). The distal link button 245 can be used to alter or select the control scheme of the robotic arm 200.

Figure 22:
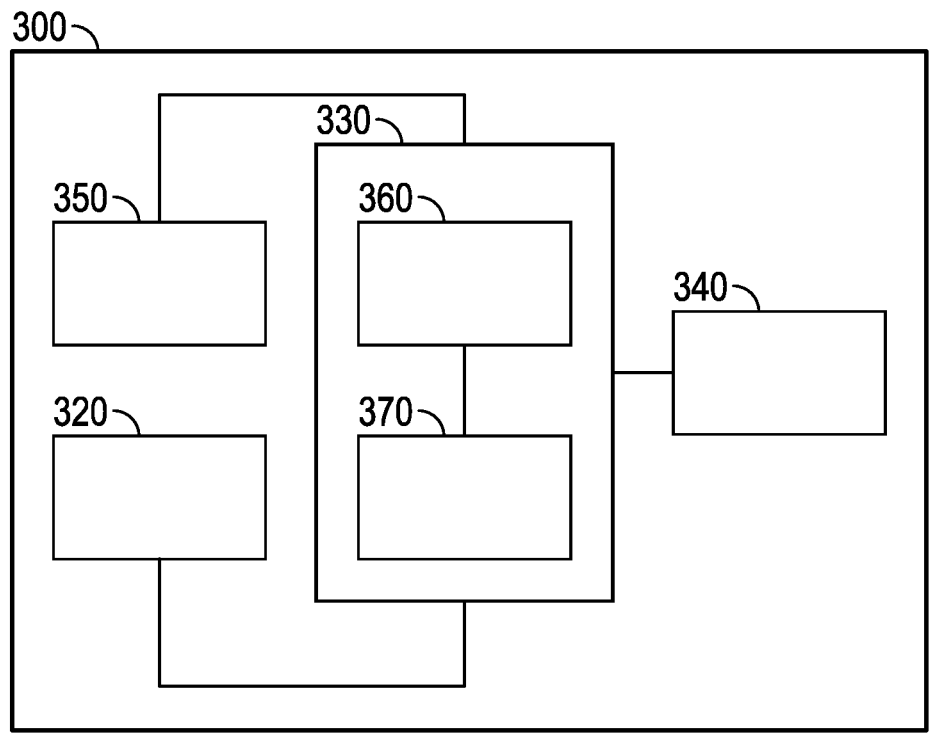
FIG. 22 is a schematic layout of a robotic arm and controller.

FIG. 22 shows a control schematic of a robotic arm 300 including one or more linkages coupled by one or more corresponding articulable joints, similar to the robotic arm 200. The robotic arm 300 can include a motor 320 of one of the articulable joints coupled with a controller 330. The controller 330 can include a processor 360 coupled with a computer-readable memory 370.

The robotic arm 300 can include a sensor 350. The sensor 350 can be a load cell (e.g., a multi-axis force and/or torque sensor, such as load cell 250) or a force sensor (e.g., single direction force sensor, such as force sensor 241). The sensor 350 can be mounted on the robotic arm 300 to detect forces and/or torques on a distal end of the robotic arm 300. Optionally, the sensor 350 can measure the forces and/or torques. The sensor 350 can generate a signal based on the forces and/or torques. The controller 330 can receive the generated signal. The processor 360 can execute instructions stored on the computer-readable memory 370 based on the signal received from the sensor 350. The executed instructions can generate a motor control signal for operating the motor 320 in accordance with one or more of the control schemes described below. The motor 320 can receive the motor control signal and move the linkage based on the motor control signal.

The robotic arm 300 can further include an input 340. The input 340 can be a button (e.g., buttons 242, 244, or 245) and/or a cannula detection sensor (e.g., cannula detection sensor 243). The input 340 can receive a user input or another status of the robotic arm. The controller 330 can receive an input signal from the input 340. The control scheme for which the motor control signal is generated can be based on the input signal from the input 340. In certain implementations, the control scheme can be selected based on the button actuated, the docked or undocked state of the cannula, and/or the currently operating control scheme of the robotic arm. The executed instructions can generate the motor control signal for operating the motor 320 further based on the user input signal.

B. Robotic Arm Control Schemes

The robotic arm 200 can be operated in a number of different control schemes or modes. The control schemes can variously support tele-operation and/or direct manual manipulation of the robotic arm 200. The exemplary control schemes include:

i. Arm Position Control.

The arm position control scheme can be used for remote tele-operation ("primary usage") of the robotic arm 200. In the arm position control scheme, position inputs are received at the physician console (e.g., controller 182) from a clinician. The position inputs are translated into a position of the robotic arm using reverse kinematics and/or kinetics and/or a scaling factor. The reverse kinematics and/or kinetics can include a virtual (e.g., mathematical) model of the robotic arm 200. The virtual model can model the series of linkages and articulable joints of the robotic arm 200. The virtual model can model the medical instrument driver 230 and the medical instrument 235. The virtual model can include one or more constraints for the virtual robotic arm, such as remote centers of motion for the medical instrument 235, and/or other objects located within an operable space for the robotic arm (e.g., other robotic arms, patients, or other medical equipment).

Based on the virtual model, a controller can generate one or more motor control signals to move the articulable joints and/or medical instrument driver into the translated position of the robotic arm. Motors of the corresponding articulable joints and/or medical instrument driver can be controlled based on the motor control signals.

Figure 23:
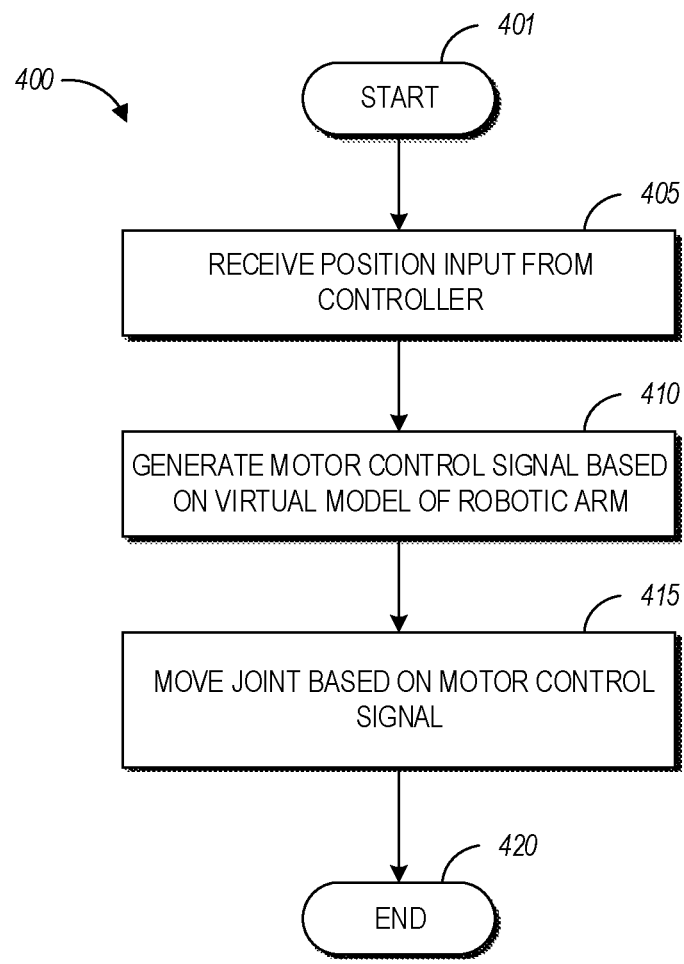
FIG. 23 shows a flow chart of a method of controlling a surgical robotic arm in an arm position control mode.

Tele-operation of the robotic arm 200 in the arm position control scheme is illustrated by the process 400 shown in FIG. 23. At step 401, the process 400 can start. The process 400 can start based on an input form a user, powering on the robotic arm 200, docking with a cannula or other criteria. At step 405, the controller can receive a positional change for the robotic arm 200 from the physician console. At step 410, the controller can generate a motor control signal based on the virtual model of the robotic arm to effect the positional change. At step 415, the motor of an articulable joint can receive the motor control signal to move the robotic arm in accordance with the control signal (based on the positional change). At step 420, the process 400 can end. The process 400 can end based on a user input, power off the robotic arm, detecting a criteria for entering a different control scheme (such as direct manual manipulation of the robotic arm), or other criteria.

The arm position control scheme can also be used to hold the robotic arm in a firm pose ("secondary usage"). In the firm pose mode, the robotic arm 200 receives no position inputs for moving the robotic arm. Accordingly, the controller can generate one or more motor control signals to maintain the positions of the articulable joints and medical instrument driver.

The robotic arm can operate in the arm position control scheme when it is either docked or undocked to a cannula. When docked to a cannula, the robotic arm can be operated in the arm position control scheme for teleoperation. In this control mode, the robotic arm can intraoperatively perform remote-center robotic laparoscopy (e.g., robotically-enabled medical system 36), or virtual rail endoscopy (e.g., the robotically-enabled system 10). When the robotic arm is undocked to a cannula, the arm position control scheme can be used to hold the robotic arm in the firm pose.

ii. Admittance Control.

The admittance control scheme allows the robotic arm 200 to move in response to a force (i.e., force (non-rotational) and/or torque (rotational)) on the robotic arm 200. The force can be detected by a sensor, such as the load cell 250 or the A0 force sensor. The sensor can measure the force acting on a portion of the robotic arm 200 distal to the sensor. The sensor can generate a signal indicating the force to the controller of the robotic arm 200. The controller can receive the signal and generate a motor control signal based on the measured force. A motor of a joint of the robotic arm can receive the motor control signal and move a linkage in response thereto. The movement of the linkage can correspond to direction and/or magnitude of the force. In certain implementations, the motor control signal can move the joint in the direction of the force. Optionally, multiple joints of the robotic arm can be moved in the direction of the force.

Under the admittance control scheme, the robotic arm can assist the user in moving the robotic arm by driving one or more motors associated with the controller to result in the desired velocities and/or positions of the robotic arm. Accordingly, in some implementations, a robotic arm under admittance control may hide the perceived inertia of the robotic arm 200. The motors of the articulable joints can help to accelerate the mass of the articulable links and linkages based on the force input (e.g., based on the motor control signal). In contrast, in an impedance control scheme in which the articulable joints are back driven, the user maybe responsible for all mass acceleration. Accordingly, in some embodiments, the robotic arm can feel lighter in the admittance control scheme than in an impedance control scheme.

The admittance control scheme can be initiated with a button, such as the button 242 (e.g., donut button). In certain implementations, the admittance control scheme can be initiated solely by the button. When the button is release (as in a press-and-hold configuration) or toggled off, the robotic arm can revert to the arm position control scheme. In other implementations, the admittance control scheme can be initiated based on detected forces (e.g., over a threshold). The admittance control scheme can be disabled after a period of inactivity, forces falling below the threshold (e.g., for a period of time), or other criteria.

Figure 24:
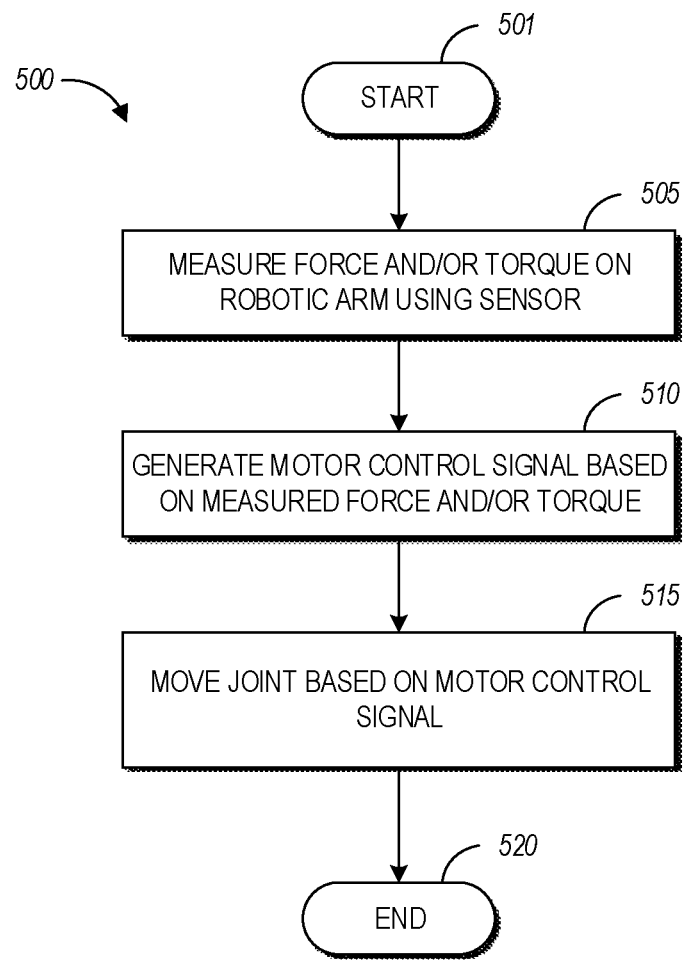
FIG. 24 shows a flow chart of a method of controlling a surgical robotic arm in an admittance control mode.

The admittance control scheme for the robotic arm 200 is illustrated by the process 500 shown in FIG. 24. At step 501, the process 500 can start. The process 500 can start based on detecting a force on the robotic arm 200 using a sensor such as the load cell 250 or the force sensor 241. In some embodiments, the force can be compared to a threshold force. The force can be from and/or indicate direct manual manipulation of the robotic arm 200. The process 500 can start based on receiving a user input such as through the buttons 242, 244, or 245.

At step 505, the sensor can measure the force on the robotic arm. At step 510, a controller can generate a motor control signal based on the force measured by the sensor. The motor control signal can be configured to move the robotic arm 200 in the direction of the force. At step 515, the motor of an articulable joint can receive the motor control signal to move the robotic arm accordingly.

At step 520, the process 500 can end. The process 500 can end based on the force falling below the threshold, detecting no force on the robotic arm 200, a user input (such as through buttons 242, 244, 245), detecting a criteria for entering a different control scheme (such as direct manual manipulation of the robotic arm), and/or other criteria.

The robotic arm 200 can be under admittance control when undocked to a cannula (e.g., for last-mile docking/undocking motion), as well as when it is docked to a cannula (e.g., for adjusting a remote center of motion for the medical instrument 235 i.e., port bumping and/or slave clutching). For example, a clinician may want to complete the docking of the robotic arm to a cannula. The user can push the button 242 thereby activating admittance control mode.

Figure 25:
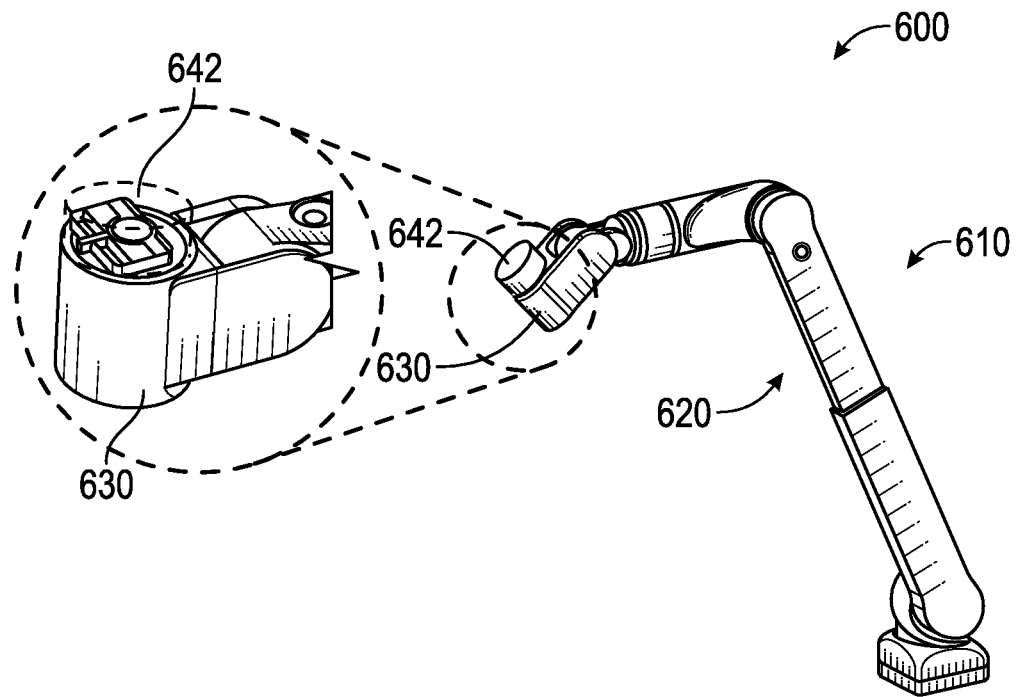
FIG. 25 another embodiment of a robotic arm including a grab point.

The admittance control scheme can also be based on a grab point mounted on a load cell. FIG. 25 shows another embodiment of a robotic arm 600. The robotic arm 600 can include a plurality of linkages 620 coupled by corresponding articulable joints 610. The robotic arm 600 can include a grab point 642. The grab point 642 can be located on or adjacent to a medical instrument driver 630. The grab point 642 can be mounted on a load cell (e.g., a 3 or 6 axis load cell). A clinician can activate the admittance control schemed by grabbing the grab point 642. The load cell can detect forces on the grab point 642 to open the admittance control scheme. The load cell can then measure force on the grab point to allow the clinician the manually manipulate the robotic arm. The clinician can be assisted by motors driving the articulable joints 610. This assistance in the admittance control scheme can assist the clinician to dock with a cannula and/or perform other fine movements of the robotic arm 600.

The robotic arm can be operated by switching between the admittance control scheme and the arm position control scheme. For example, the robotic arm can be operated tele-operatively, until a trigger, such as a user input initiates admittance control. Admittance control can operate until another trigger, such as release of a user input, re-initiates arm position control. In this manner, a clinician can seamlessly switch between these two modes.

The arm position control scheme and the admittance control scheme can be used for different steps in a medical procedure. For example, the admittance control can be used for larger movements of the robotic arm (e.g., folding), movement of remote centers of motion, connection with a cannula, etc. The arm position control scheme can be used for performing medical procedures. Both arm position control and admittance control can be used in conjunction with various nullspace control schemes, as described below.

The different inputs (e.g., buttons 242, 244, 245) may place the robotic arm under different control modes, depending on the state of the robotic arm. For example, when the robotic arm 200 is docked to a cannula (as detected by the cannula detection sensor 243), actuating an input (e.g., a button) may place the robotic arm is an admittance nullspace control mode (e.g., to allow for slave clutching when docked). In some embodiments, admittance nullspace control mode is not activated by an input in the form of button, but rather by applying force to the robotic arm such that it meets or exceeds a threshold force. Conversely, when the robotic arm 200 is undocked to a cannula (as detected by the cannula detection sensor 243), actuating an input may place the robotic arm is an active admittance mode (e.g., to allow for positioning of the medical instrument).

iii. Collision Avoidance Nullspace Control (Kinematics Based).

Nullspace motion is allowed where robotic arms include redundant links or excess degrees for freedom for a given position of an attached medical instruments. Accordingly, one or more of the linkages of the robotic arms can move within a nullspace while maintaining the position of the end effector of the medical instruments. Under the collision avoidance nullspace control scheme, collisions between the robotic arm 200 and other robotic arms (or other components) in the surgical robotic system are detected using virtual models (e.g., kinematic and/or kinetic models of the robotic arm 200) and avoided automatically by using nullspace motion of at least one robotic arm. Accordingly, inter-arm collision and/or intra-arm collisions can be prevented in the collision avoidance nullspace control scheme.

The collision avoidance nullspace control scheme can be enabled when either the arm position control scheme or admittance control scheme is enabled. The collision avoidance nullspace control scheme can be available during tele-operation and/or manual manipulation of the robotic arm. The collision avoidance nullspace control scheme can be a fully autonomous mode (e.g., the robotic system itself will detect an impending collision between two arms and will move one or more joints of one or more of the arms to avoid collision automatically).

Figure 26A:
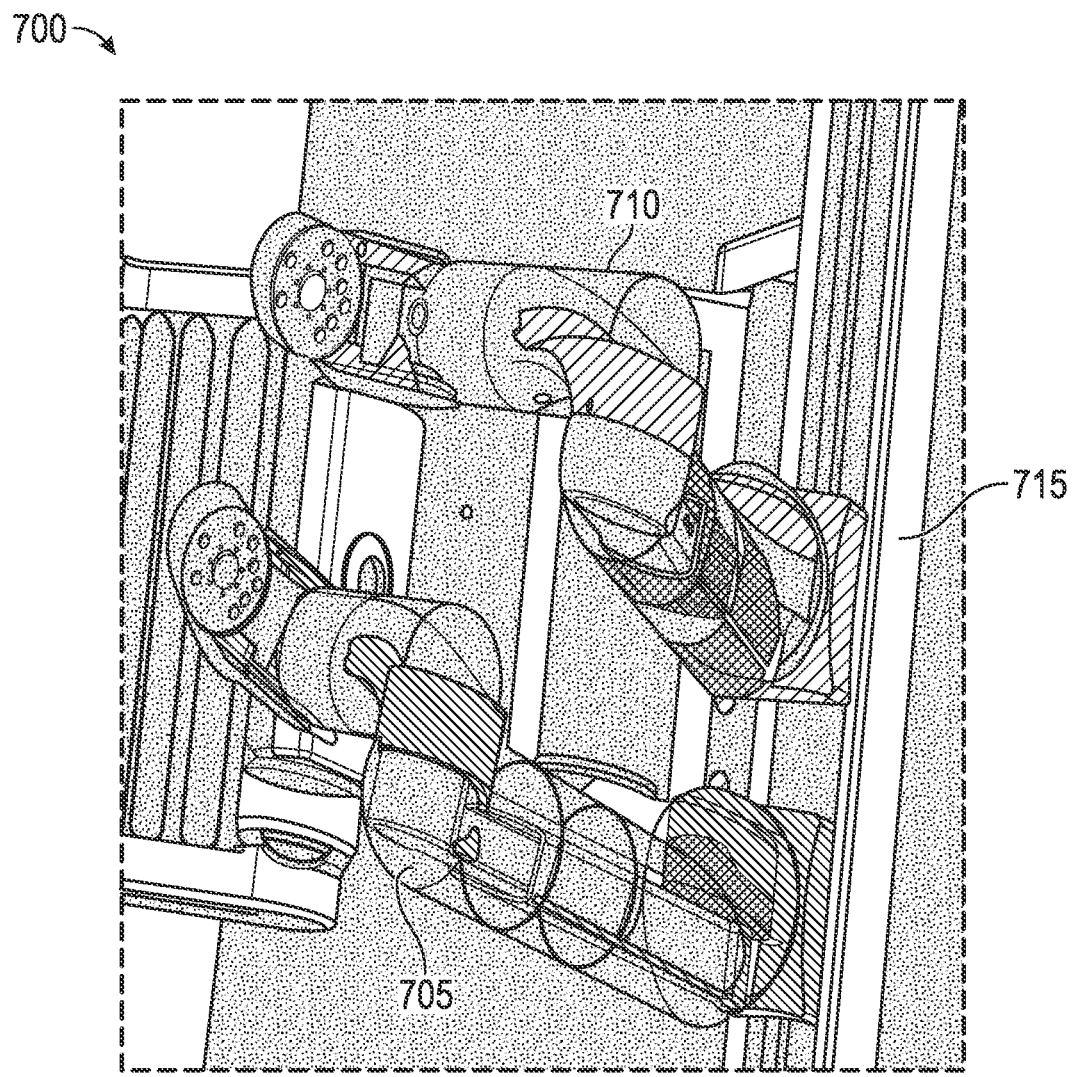
FIGS. 26A-B illustrate an example sequence of nullspace collision avoidance.
Figure 26B:
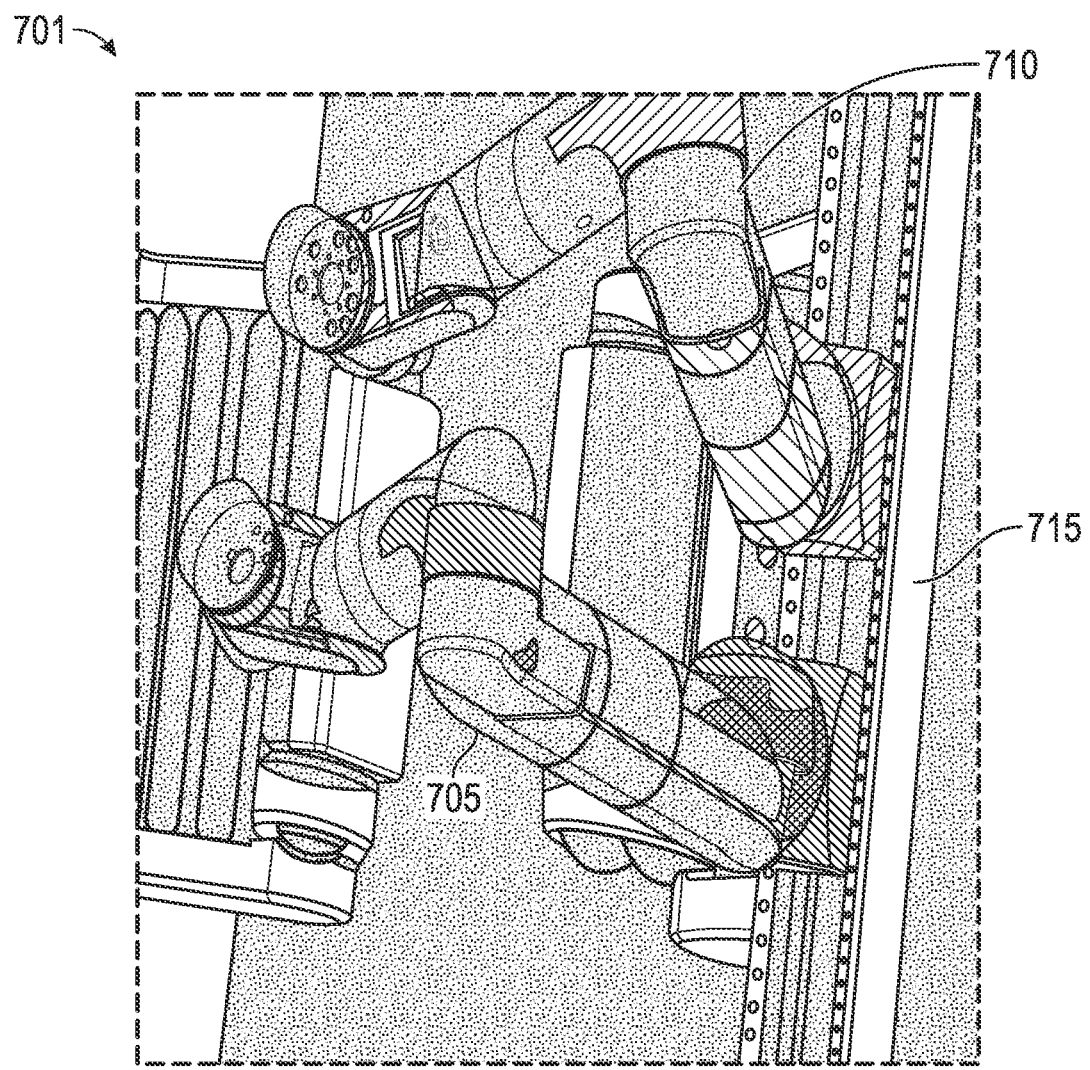

FIGS. 26A and 26B illustrate an example sequence of actions under the collision avoidance nullspace control scheme. At an initial point in time 700 illustrated in FIG. 26A, the system is moving a first robotic arm 705 and the associated first medical instrument based on a commanded movement towards a second robotic arm 710 along a support rail 715 (e.g., in either the arm position control scheme or admittance control scheme). The second robotic arm can include a second medical instrument. Movement of the first robotic arm 705 may bring certain points on the first and second robotic arms 705 and 710 into collision based on virtual models of the system.

Accordingly, in the collision avoidance nullspace control scheme, when the first and second robotic arms 705, 710 come within a trigger distance, one or more joints of the first and second robotic arms 705, 710 can automatically adjust within the nullspace (e.g., via its redundant joints) to avoid a collision, as shown in the image of the subsequent point in time 701 in FIG. 26B. As shown in FIG. 26B, the base joint of the second robotic arm 710 is slid along the support rail 715, thereby providing collision avoidance via null space movement (e.g., without moving the end effector of the medical instrument associated with the second robotic arm 710). As shown in FIG. 26B, that the end effector of the second medical instrument associated with the second robotic arm 710 has not moved-only the proximal joints for null space motion and collision avoidance have moved.

Figure 27:
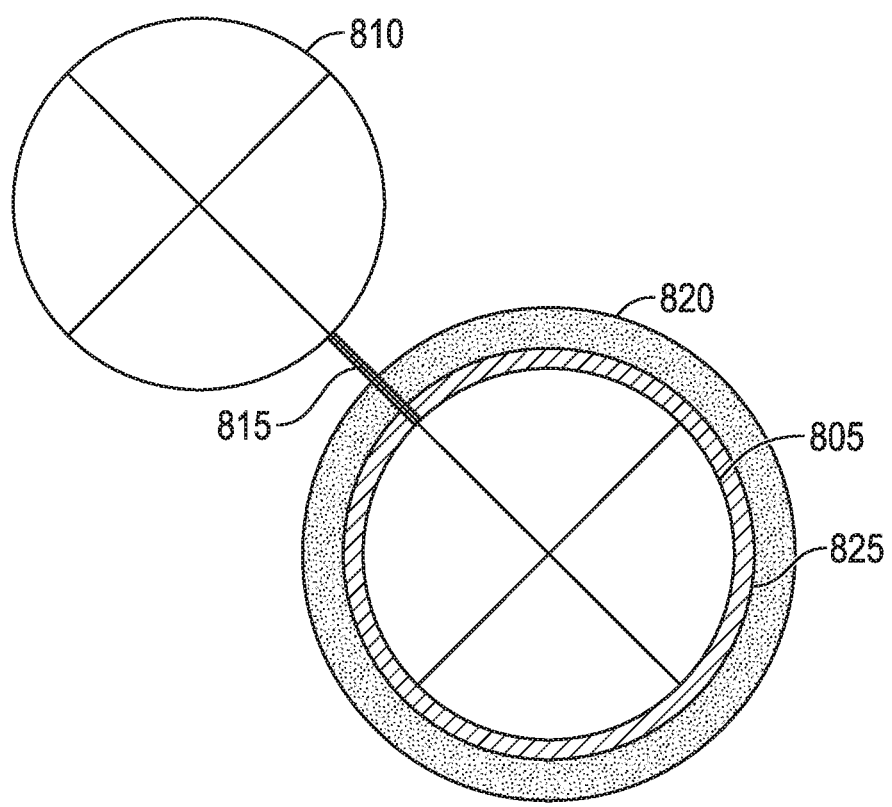
FIG. 27 illustrates a trigger distance for nullspace collision avoidance.

FIG. 27 illustrates the cutoff and trigger distances for a modeled link in accordance with aspects of this disclosure. In particular, FIG. 27 illustrates the cross-sections of a first link 805 and a second link 810 which are separated by a current (minimum) distance 815. A trigger distance 820 and a cutoff distance 825 are shown surrounding the first link 805. Although not illustrated, the second link 810 may also have a trigger distance and a cutoff distance, which may or may not have the same values as the trigger distance 820 and the cutoff distance 825 associated with the first link 805. As described herein, when another link (such as the second link 810) penetrates the trigger distance 820 of the first link 805, the system may take an action to avoid collision with the other link.

In certain implementations, the system can include a haptic feedback system for the clinician (e.g., using tele-operation or manual manipulation). As the robotic arm being moved approaches a collision with another object, the system increases a resistance of one or more joints of the robotic arm to movement towards the object. As the proximity increases, the resistance can increase.

If the system detects that an arm has two opposing collisions, then the system may not be able to avoid the collision with null space motion and the system will stop motion once the cutoff distance has been hit. When the system prevents further motion due to a cutoff distance breach, the system can provide haptic force feedback to the user to inform the user of the need to move one of the tools in the opposite direction to allow the other to move away from the collision.

iv. Admittance Nullspace Control (Force or Torque-Based).

In the admittance nullspace control scheme, forces acting on the robotic arm 200 can move one or more linkages within a nullspace. Unlike the collision avoidance nullspace control scheme that is based on kinematics (e.g., a distance of separation between two robotic arms), the admittance nullspace control scheme relies on actual external force being applied to one or more robotic arms. For example, the force applied to the robotic arm 200 can be a user caught between robotic arms of the system, an accessory is found to be in the way of a robotic arm sliding on the support rail 220, or a clinician creating patient access.

The admittance nullspace control scheme can be initiated in various ways. In one exemplary implementation, a clinician can approach a bed, and push a touchpoint on the robotic arm and thereby initiate the admittance nullspace control scheme. In another implementation, a clinician can apply a force above a threshold on a contact portion of the robotic arm (e.g., its links). The force can initiate the admittance nullspace control scheme, although the same level of force may be required to remain in the scheme.

In the admittance nullspace control scheme, a force sensor (such as the force sensor 241) can be placed at the A0 base joint of the robotic arm 200. The force sensor can measure external forces that are applied along the support rail 220. If nullspace movement of the robotic arm 200 is available, the controller can generate a motor control signal based on the measured forces and move one or more of the articulable joints based on the motor control signal. If nullspace movement of the robotic arm 200 is unavailable or there is a risk of collision with an adjacent arm, the controller can prevent movement of the robotic arm. The controller can also provide haptic feedback to alert the user. The haptic feedback can have an upper threshold in order to overcome autonomous collision-avoidances on multiple arms, instead of being rigidly overpowered or causing unintended collisions.

The admittance nullspace control scheme can provide artificial compliance of a robotic arm during the active control scheme via either tele-operation or manual manipulation, such as in the admittance control scheme. Accordingly, in some implementations, both of these modes can work in concert to provide automated nullspace control of the robotic arms. By tuning and saturating both nullspace controls, a safe force interaction with any robotic arm can be created for all the arms in the space to deform in their respective nullspaces.

v. Nullspace Jogging Control (Button Based).

In a nullspace jogging control scheme, a clinician can move the robotic arm 200 along one degree of freedom within a nullspace based on a user input. One or more user inputs (e.g., proximal link button 244), can be provided for activation of the nullspace jogging control scheme. In the nullspace jogging control scheme, a clinician can adjust the surgical robotic system to, for example, accommodate patient movement, medical equipment or other aspects of a medical procedure.

In one example, nullspace jogging control scheme allows movement of the robotic arm 200 in the direction of the support rail 220. The scheme can be initiated by pressing the proximal link button 244. Once initiated, the force sensor 241 can detect forces acting on the proximal link to control a motor to assist movement of the robotic arm 200 along the support rail 220. Alternatively, two input buttons can be included instead of a force sensor. Each button can move in a different direction along the support rail 220.

Some of the control schemes can operate in conjunction with other control modes. For example, the collision avoidance nullspace control, admittance nullspace control, and/or nullspace jogging control scheme can operate during arm position control or admittance control. Advantageously the collision avoidance nullspace control and the admittance nullspace control can operate automatically to reduce collisions between both known (e.g., kinematic) system components and unknown components (e.g., adjacent environmental structures contacted by robotic arm). Accordingly, the various modes can enhance safe operation of the medical or surgical robotic systems.

3. Implementing Systems and Terminology.

Implementations disclosed herein provide systems, methods and apparatus for admittance based control schemes.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The control functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A surgical robotic system, comprising:
   a robotic arm comprising:
      a proximal end and a distal end;
      a plurality of linkages coupled by a plurality of joints between the proximal and distal ends;
      one or more motors coupled with at least one joint of the plurality of joints and configured to adjust a position of at least one linkage of the plurality of linkages;
      a sensor coupled with the robotic arm;
      an input positioned on the robotic arm and configured to be activated by a user;
   a processor; and
   a memory storing computer-executable instructions to cause the processor to:
      measure a force on the robotic arm with the sensor, the force located distal to the sensor;
      generate a signal based on the measured force;
      control the one or more motors based on the signal to move the at least one linkage of the plurality of linkages;
      receive a user input signal generated by activation of the input by the user; and
      control the one or more motors to move the at least one linkage further in response to receiving the user input signal.

2. The surgical robotic system of claim 1, wherein movement of the at least one linkage in response to the force is within a nullspace of the robotic arm without moving a medical instrument supported by the robotic arm, the robotic arm including a redundant degree of freedom for positioning the medical instrument.

3. The surgical robotic system of claim 2, wherein the redundant degree of freedom is along a support rail supporting the robotic arm.

4. The surgical robotic system of claim 3, wherein movement along the support rail is initiated by an input.

5. The surgical robotic system of claim 2, wherein movement of the at least one linkage in the nullspace is based on modelling a position of the at least one linkage in a virtual model of the robotic arm.

6. The surgical robotic system of claim 1, further comprising a second robotic arm supporting a second medical instrument;
   wherein the computer-executable instructions are further configured to cause the processor to:
      measure a position of a second robotic arm;
      generate a second signal based on the position of the second robotic arm; and
      control one or more motors of the second robotic arm based on the second signal to move a second linkage of the second robotic arm,
   wherein the movement of the second linkage is within a nullspace of the second robotic arm without moving the second medical instrument, the second robotic arm including a redundant degree of freedom for positioning the second medical instrument.

7. The surgical robotic system of claim 6, wherein generating the second signal is further based on the robotic arm being within a trigger distance of the second robotic arm.

8. The surgical robotic system of claim 1, wherein the computer-executable instructions are further configured to cause the processor to:
   increase a resistance of the at least one joint to movement in a first direction based on a proximity of the robotic arm to an adjacent structure.

9. The surgical robotic system of claim 1, wherein the input is a button on the robotic arm.

10. The surgical robotic system of claim 1, wherein the input is on the distal end of the robotic arm.

11. The surgical robotic system of claim 10, wherein the input is a button on an instrument drive mechanism.

12. The surgical robotic system of claim 1, wherein the memory further comprises computer-executable instructions to cause the processor to:
compare the force measured with the sensor to a threshold force; and
control the one or more motors to move the at least one linkage further in response to the force being above the threshold force.

13. The surgical robotic system of claim 12, wherein the sensor is a load cell and bridges a structural break in the linkage and the threshold force is based, at least in part, on a mass of the robotic arm and forces of gravity.

14. The surgical robotic system of claim 12, wherein the sensor includes a load cell coupled with a grab point on the distal end of the robotic arm.

15. The surgical robotic system of claim 1, wherein the distal end of the robotic arm further comprises an instrument drive mechanism configured to couple with a medical instrument.

16. The surgical robotic system of claim 15, wherein the force is configured to adjust alignment of the medical instrument.

17. The surgical robotic system of claim 15, wherein movement of the at least one linkage adjusts a position of a remote center of motion of the medical instrument.

18. The surgical robotic system of claim 15, wherein controlling the one or more motors to move the at least one linkage further includes controlling at least two of the plurality of joints to move in a first direction.

19. A surgical robotic system, comprising:
a robotic arm comprising:
  a proximal end and a distal end;
  a plurality of linkages coupled by a plurality of joints between the proximal and distal ends;
  one or more motors coupled with at least one joint of the plurality of joints and configured to adjust a position of at least one linkage of the plurality of linkages; and
  a sensor coupled with the robotic arm;
a processor; and
a memory storing computer-executable instructions to cause the processor to:
  measure a force on the robotic arm with the sensor, the force located distal to the sensor;
  generate a signal based on the measured force;
  control the one or more motors based on the signal to move the at least one linkage of the plurality of linkages; and
  increase a resistance of the at least one joint to movement in a first direction based on a proximity of the robotic arm to an adjacent structure.

20. A surgical robotic system, comprising:
a robotic arm comprising:
  a proximal end and a distal end;
  a plurality of linkages coupled by a plurality of joints between the proximal and distal ends;
  one or more motors coupled with at least one joint of the plurality of joints and configured to adjust a position of at least one linkage of the plurality of linkages;
  a sensor coupled with the robotic arm; and
  a cannula detection sensor configured to detect a docked/undocked state of the robotic arm to a cannula;
a processor; and
a memory storing computer-executable instructions to cause the processor to:
  measure a force on the robotic arm with the sensor, the force located distal to the sensor;
  generate a signal based on the measured force;
  control the one or more motors based on the signal to move the at least one linkage of the plurality of linkages;
  receive a cannula input signal from the cannula detection sensor; and
  control the one or more motors to move the at least one linkage further in response to receiving the cannula input signal and the measured force on the robotic arm.

* * * * *